(12) United States Patent
Vasyltsov et al.

(10) Patent No.: US 10,178,974 B2
(45) Date of Patent: Jan. 15, 2019

(54) METHOD AND SYSTEM FOR MONITORING CONTINUOUS BIOMEDICAL SIGNAL

(71) Applicant: SAMSUNG ELECTRONICS CO., LTD., Suwon-si, Gyeonggi-do (KR)

(72) Inventors: Ihor Vasyltsov, Suwon-si (KR); Seung-Hwan Lee, Seoul (KR); Jae-Yong Park, Seongnam-si (KR); Jang-Su Lee, Seoul (KR); Ji-Su Kim, Seoul (KR); Seung-Jin Kim, Suwon-si (KR); Jun-Yeon Lee, Hwaseong-si (KR)

(73) Assignee: Samsung Electronics Co., Ltd., Suwon-si, Gyeonggi-do (KR)

( * ) Notice: Subject to any disclaimer, the term of this patent is extended or adjusted under 35 U.S.C. 154(b) by 91 days.

(21) Appl. No.: 15/352,889

(22) Filed: Nov. 16, 2016

(65) Prior Publication Data

US 2017/0164907 A1    Jun. 15, 2017

(30) Foreign Application Priority Data

Dec. 14, 2015 (KR) ........................ 10-2015-0178521

(51) Int. Cl.
*A61B 5/00* (2006.01)
*A61B 5/0402* (2006.01)
(Continued)

(52) U.S. Cl.
CPC .......... *A61B 5/7282* (2013.01); *A61B 5/0022* (2013.01); *A61B 5/0024* (2013.01); (Continued)

(58) Field of Classification Search
CPC ....... A61B 5/0022; A61B 5/0024; A61B 5/01; A61B 5/02405; A61B 5/02416;
(Continued)

(56) References Cited

U.S. PATENT DOCUMENTS

| 5,394,879 A | 3/1995 | Gorman |
| 5,400,794 A | 3/1995 | Gorman |

(Continued)

FOREIGN PATENT DOCUMENTS

| JP | 2013-121440 A | 6/2013 |
| KR | 10-0723655 | 5/2007 |

(Continued)

OTHER PUBLICATIONS

Lobodzinski, S. Suave, "ECG Patch Monitors for Assessment of Cardiac Rhythm Abnormalities," Progess Cardiovascular Diseases 56 (2013) 224-229.

(Continued)

*Primary Examiner* — John H Le
(74) *Attorney, Agent, or Firm* — Volentine, Whitt & Francos, PLLC

(57) ABSTRACT

A method and system for monitoring a biomedical signal employ a sensor module configured to output a continuous electrical signal by sensing the biomedical signal, a memory configured to store reference data, a transmitter configured to transmit output data via a wireless channel, and a data processing unit configured to determine whether to transmit input data via the transmitter as the output data, based on the input data, which is generated from the continuous electrical signal, and the reference data.

20 Claims, 25 Drawing Sheets

(51) Int. Cl.

| | | |
|---|---|---|
| A61B 5/053 | (2006.01) | |
| A61B 5/0496 | (2006.01) | |
| A61B 5/0488 | (2006.01) | |
| A61B 5/01 | (2006.01) | |
| A61B 5/024 | (2006.01) | |
| A61B 5/0476 | (2006.01) | |
| G06F 19/00 | (2018.01) | |
| G16H 40/67 | (2018.01) | |

(52) U.S. Cl.
CPC ............ *A61B 5/7232* (2013.01); *G06F 19/00* (2013.01); *G16H 40/67* (2018.01); *A61B 5/01* (2013.01); *A61B 5/02405* (2013.01); *A61B 5/02416* (2013.01); *A61B 5/0402* (2013.01); *A61B 5/0476* (2013.01); *A61B 5/0496* (2013.01); *A61B 5/04884* (2013.01); *A61B 5/0531* (2013.01); *A61B 5/7225* (2013.01); *A61B 5/7405* (2013.01); *A61B 5/7455* (2013.01)

(58) Field of Classification Search
CPC . A61B 5/0402; A61B 5/0476; A61B 5/04884; A61B 5/0496; A61B 5/0531; A61B 5/7225; A61B 5/7232; A61B 5/7282; A61B 5/7405; A61B 5/7455
USPC ......... 702/189; 375/224, 295; 600/300, 484, 600/520, 509
See application file for complete search history.

(56) References Cited

U.S. PATENT DOCUMENTS

| | | |
|---|---|---|
| 5,538,007 A | 7/1996 | Gorman |
| 5,913,827 A | 6/1999 | Gorman |
| 6,208,889 B1 | 3/2001 | Gorman |
| 6,304,774 B1 | 10/2001 | Gorman |
| 8,519,867 B2 | 8/2013 | Palmer et al. |
| 8,548,174 B2 | 10/2013 | Dufresne et al. |
| 8,594,772 B2 | 11/2013 | Eggenberger et al. |
| 8,718,938 B2 | 5/2014 | Wolf et al. |
| 2008/0281165 A1 | 11/2008 | Rai et al. |
| 2010/0082302 A1* | 4/2010 | Garudadri ............ A61B 5/0006 702/189 |
| 2010/0246651 A1 | 9/2010 | Baheti et al. |
| 2011/0136536 A1 | 6/2011 | Garudadri et al. |
| 2012/0123226 A1 | 5/2012 | Schwenk et al. |
| 2012/0263082 A1 | 10/2012 | Garudadri et al. |
| 2013/0035571 A1 | 2/2013 | Moure Alonso et al. |
| 2013/0115885 A1 | 5/2013 | Schmitt |
| 2013/0237868 A1 | 9/2013 | Choi et al. |
| 2014/0145859 A1 | 5/2014 | Eggenberger et al. |
| 2014/0159912 A1 | 6/2014 | Fraden |
| 2014/0244278 A1 | 8/2014 | Park et al. |
| 2015/0105677 A1 | 4/2015 | Nagasaki et al. |

FOREIGN PATENT DOCUMENTS

| | | |
|---|---|---|
| KR | 10-1192848 B1 | 10/2012 |
| WO | WO 2012-011031 A1 | 1/2012 |

OTHER PUBLICATIONS

Padma, Tatiparti, "ECG compression and labview implementation," J. Biomedical Science and Engineering, 2009, 2, 177-183.

Joseph, Bastin, "A Low Complexity On-Chip ECG Data Compression Methodology Targeting Remote Health-Care Applications," 2014 IEEE, pp. 5944-5947.

Biswas, Dwaipayan, "ECG Compression for Remote Healthcare Systems using Selective Thresholding based on Energy Compaction," 2012 IEEE.

Dementyev, Artem, "Power Consumption Analysis of Bluetooth Low Energy, ZigBee and ANT Sensor Nodes in a Cyclic Sleep Scenario," Wireless Symposium (IWS), 2013 IEEE International (Apr. 2013).

* cited by examiner

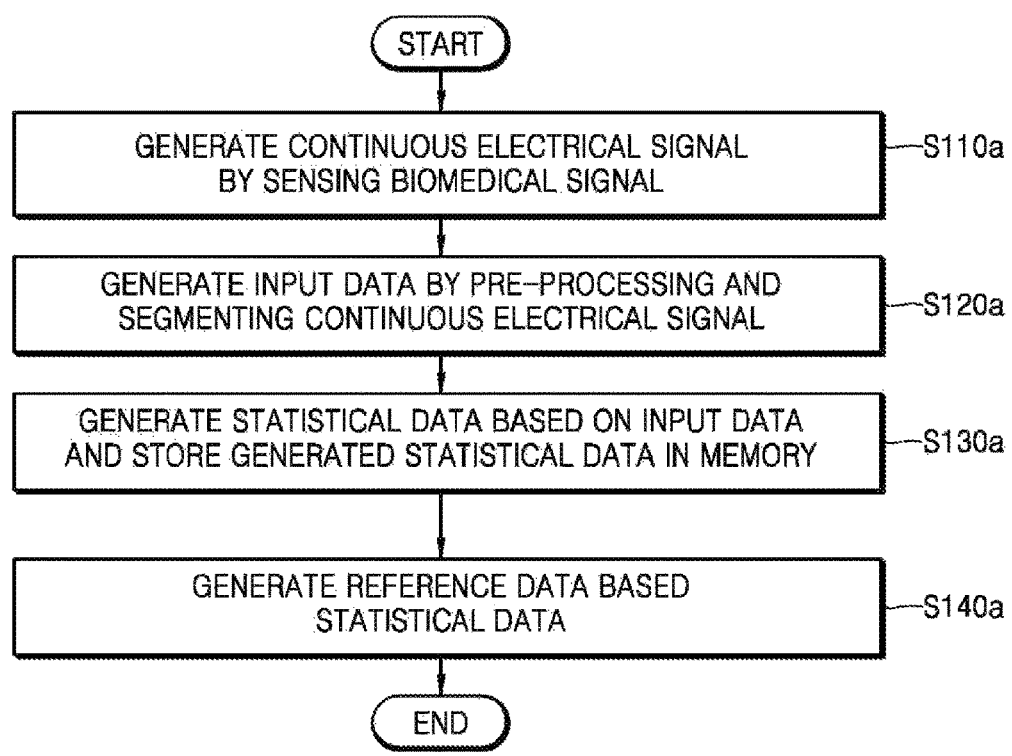

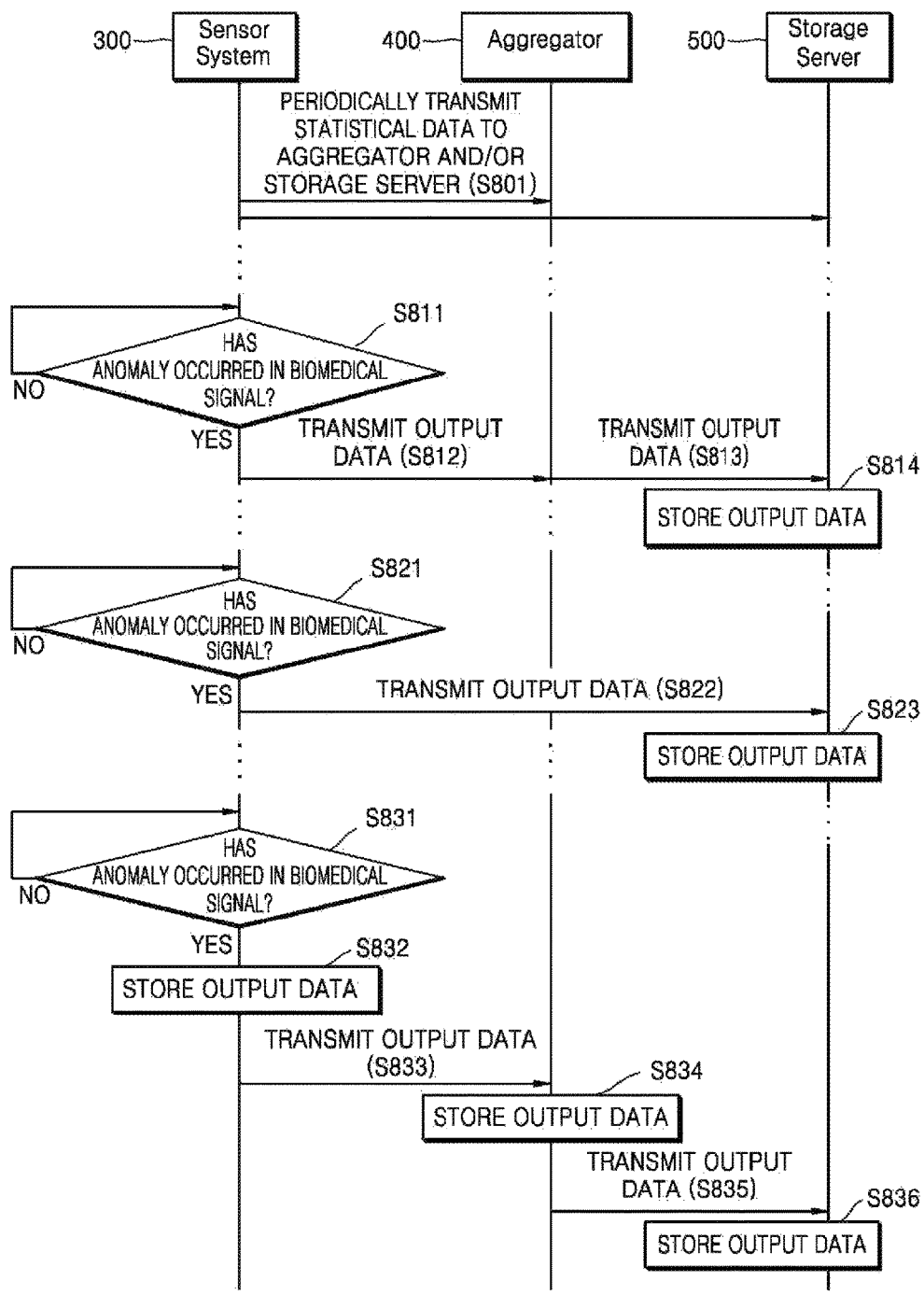

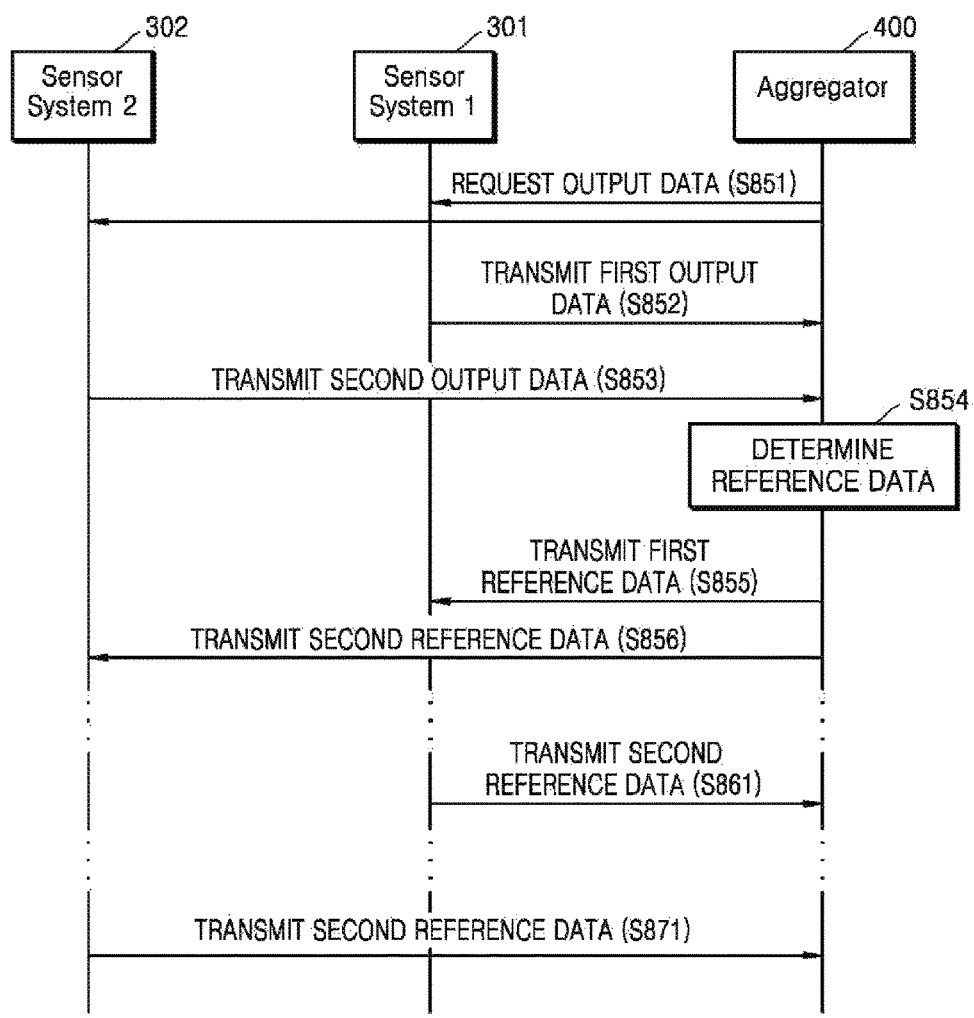

METHOD AND SYSTEM FOR MONITORING CONTINUOUS BIOMEDICAL SIGNAL

CROSS-REFERENCE TO RELATED APPLICATION

This application claims the benefit of Korean Patent Application No. 10-2015-0178521, filed on Dec. 14, 2015, in the Korean Intellectual Property Office, the disclosure of which is incorporated herein in its entirety by reference.

BACKGROUND

The inventive concept relates to a method and system for monitoring a biomedical signal, and more particularly, to a method and system for continuously monitoring a biomedical signal.

A signal that is used to obtain information from a living person or animal may be referred to as a biomedical signal. Numerous physiological processes that are performed in the body of a person or animal may generate various types of biomedical signals, including a biomedical chemical signal, an electrical signal, a physical signal, and the like. Continuously monitoring a biomedical signal may be important in sensing a change in a body that produces the biomedical signal.

The biomedical signal may be sensed by a sensor (or a biomedical signal sensor), and desired information may be obtained by processing the sensed biomedical signal. The sensor that is attached to, or implanted in, a body to sense the biomedical signal may be driven by a battery, and thus, the sensor may have a finite operating time. Accordingly, it would be desirable to provide a sensor having low power consumption to continuously monitor a biomedical signal.

SUMMARY

The inventive concept provides a method of monitoring a biomedical signal, which may reduce the power consumption of a biomedical signal sensor.

The inventive concept provides a system for monitoring a biomedical signal, which may reduce the power consumption of a biomedical signal sensor.

According to an aspect of the inventive concept, there is provided a sensor system for monitoring a biomedical signal, the sensor system including: a sensor module configured to sense the biomedical signal and output a continuous electrical signal; a memory configured to store reference data; a transmitter configured to transmit output data via a wireless channel to an external device; and a data processing unit configured to determine whether to transmit input data via the transmitter as the output data, based on the input data, which is generated from the continuous electrical signal, and the reference data.

According to another aspect of the inventive concept, there is provided a method of monitoring a biomedical signal by using a sensor system in which wireless data transmission can be performed, the method including: generating a continuous electrical signal by sensing the biomedical signal; generating input data by segmenting the continuous electrical signal; determining whether to transmit the input data via a wireless channel as output data, based on the input data and previously stored reference data; and transmitting the output data via the wireless channel, if the transmission of the input data is determined.

According to another aspect of the inventive concept, there is provided a method of monitoring a biomedical signal by using at least one sensor system and an aggregator, which can communicate with each other via a wireless channel, the method including: generating, by using the at least one sensor system, input data by sensing the biomedical signal; determining, by using the at least one sensor system, whether to transmit the input data to the aggregator as output data, based on the input data and previously stored reference data; transmitting, by using the at least one sensor system, the output data to the aggregator; and transmitting, by using the aggregator, the output data to a storage server or a terminal device via a communication network after receiving the output data.

BRIEF DESCRIPTION OF THE DRAWINGS

Embodiments of the inventive concept will be more clearly understood from the following detailed description taken in conjunction with the accompanying drawings.

FIGS. 12A, 12B and 12C are flowcharts illustrating examples of operation S100 of FIG. 11.

FIG. 15 is a diagram that sequentially illustrates an example of operations between embodiments of a sensor system, an aggregator, and a storage server.

FIG. 16 is a diagram that sequentially illustrates an example of an operation between a plurality of sensor systems and an aggregator.

DETAILED DESCRIPTION OF THE EMBODIMENTS

Figure 1:
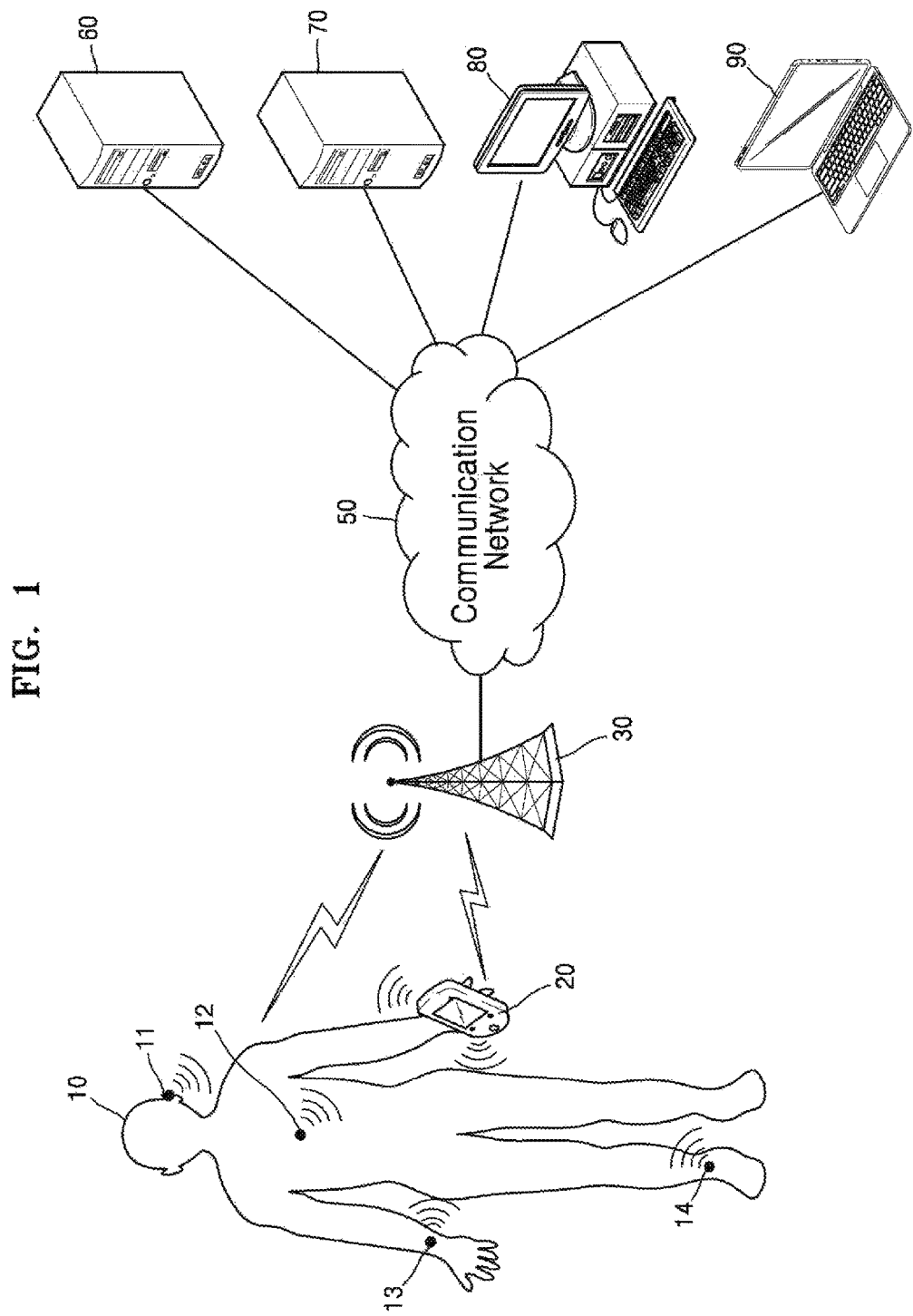
FIG. 1 is a diagram illustrating an example embodiment of an arrangement for monitoring a biomedical signal.

As used herein, the term "and/or" includes any and all combinations of one or more of the associated listed items.

The inventive concept will now be described more fully hereinafter with reference to the accompanying drawings, in which embodiments of the inventive concept are shown. These embodiments are provided so that this disclosure is thorough and complete and fully conveys the scope of the inventive concept to one skilled in the art. Accordingly, while the inventive concept can be modified in various ways and take on various alternative forms, specific embodiments thereof are shown in the drawings and described in detail below as examples. There is no intent to limit the inventive concept to the particular forms disclosed. On the contrary, the inventive concept is to cover all modifications, equivalents, and alternatives falling within the scope of the appended claims. Like reference numerals refer to like elements throughout. In the drawings, the thicknesses of layers and regions may be exaggerated for clarity.

The terminology used herein is for the purpose of describing particular embodiments only and is not intended to be limiting of the inventive concept. As used herein, the singular forms "a", "an" and "the" are intended to include the plural forms as well, unless the context clearly indicates otherwise. It will be further understood that the terms "comprises", "comprising,", "includes" and/or "including", when used herein, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless explicitly so defined herein.

FIG. 1 is a diagram illustrating an example embodiment of an arrangement for monitoring a biomedical signal.

The biomedical signal may include a biomedical chemical signal, an electrical signal, a physical signal, and the like, which are generated by various physiological processes that are performed in a body 10 of a person or animal. For example, the biomedical signal may include a photoplethysmogram (PPG), an electroencephalogram (EEG), an electromyogram (EMG), an electrooculogram (EOG), an electroretinogram (ERG), an electrogastrogram (EGG), an electrocardiogram (ECG), an electrodermal activity (EDA), a heart rate variability (HRV), a temperature, and the like. Whether a body providing a biomedical signal is abnormal may be determined by analyzing the biomedical signal.

Long-term monitoring of the biomedical signal may provide an improved diagnostic yield for the body 10. In other words, the body 10 may be more accurately diagnosed by continuously monitoring a biomedical signal in an actual life environment, such as a workspace or home, instead of temporarily diagnosing the body 10 at a hospital. To sense such a biomedical signal, one or more sensors (or biomedical signal sensors or sensor systems) may be attached to or implanted in the body 10. Referring to FIG. 1, a plurality of sensors 11, 12, 13 and 14 may be attached to or implanted in the body 10. For example, sensor 11 may be attached to the ear of the body 10 to sense a PPG, and/or sensor 12 may be attached to the chest of the body 10 to sense an ECG. As shown in FIG. 1, each of the plurality of sensors 11 to 14 may transmit data corresponding to a sensed biomedical signal to an aggregator 20 and/or an access point 30 via a wireless channel, for example, Bluetooth, ZigBee, or Wi-Fi. According to an embodiment, data that is transmitted by each of the plurality of sensors 11 to 14 to access point 30 may be encoded, and encoded data may be transmitted from access point 30 to other devices via a communication network 50.

Aggregator 20 may be a portable device that can move with the body 10, and the plurality of sensors 11 to 14 and aggregator 20 may form a body area network (BAN). For example, aggregator 20 may be a portable electronic device, such as a personal computer (PC), a tablet PC, a mobile phone, a smart phone, an e-reader, a personal digital assistant (PDA), an enterprise digital assistant (EDA), a digital still camera, a digital video camera, a portable multimedia player (PMP), a personal navigation device or portable navigation device (PND), or a handheld game console. Aggregator 20 may transmit data received from sensors 11 to 14 or data, obtained by processing data received from sensors 11 to 14, to other electronic devices 60, 70, 80, and 90 the access point 30 and communication network 50. According to an embodiment, data that is transmitted by aggregator 20 to access point 30 may be encoded, and encoded data may be transmitted to other devices via communication network 50.

Access point 30 may be referred to as a device that connects wireless communication devices to a wired network. As shown in FIG. 1, sensors 11 to 14 may transmit data corresponding to a sensed biomedical signal to other electronic devices 60, 70, 80, and 90 via access point 30 and communication network 50. Although FIG. 1 illustrates an example in which only sensor 11 communicates with access point 30, sensors 12 to 14 may also communicate with access point 30 via a wireless channel.

Each of sensors 11 to 14 may include an independent power supply and may be driven by a battery. Accordingly, sensors 11 to 14 may have finite operating times, and the operating times of sensors 11 to 14 may be extended by reducing the power consumption of sensors 11 to 14. To monitor a biomedical signal for 24 hours every day, sensors 11 to 14 may sense a biomedical signal for an operating time and transmit data corresponding to a sensed biomedical signal to aggregator 20 and/or access point 30 via a wireless channel. Transmitting data corresponding to the sensed biomedical signal may require a high bandwidth or a large storage capacity. For example, when sensor 12 sensing an ECG outputs 1024 samples, each of which includes 16 bits, every second, data that is output for 5 hours may include about 36 megabytes (MB) (i.e., 2×1024×60×60×5 bits). Since the transmission of data via a wireless channel consumes a lot of power, an operation in which sensors 11 to 14 transmit data to aggregator 20 or access point 30 may occupy a significant portion of power that is consumed by sensors 11 to 14.

The method of monitoring a biomedical signal, according to the embodiment, may extend operating times of sensors 11 to 14 by reducing the amount of data that is transmitted by sensors 11 to 14 via a wireless channel, due to characteristics of the biomedical signal, which are generally repeated in a similar form, as will be described later with reference to FIG. 2. In other words, the method of monitoring a biomedical signal, according to the embodiment, may cause sensors 11 to 14 transmit a biomedical signal via a wireless channel, if the biomedical signal is deviated from an expected range set in advance. Even if the amount of data that is transmitted via a wireless channel is reduced, the method of monitoring a biomedical signal may enable immediately checking whether a biomedical signal is abnormal, as well as accurately monitoring the biomedical signal.

Referring to FIG. 1, a plurality of communication devices may be connected to communication network 50. For example, communication network 50 may be an Ethernet network, and servers 60 and 70 and user terminals 80 and 90 as well as access point 30 may be connected to communication network 50. Servers 60 and 70 and user terminals 80 and 90 may receive data that is transmitted by sensors 11 to 14 or aggregator 20, and may acquire information about the body 10, based on the received data. Server 60 may be a storage server that stores received data, and server 70 may be a computing server that generates new data by processing received data. User terminal 80 may be a terminal installed in an emergency center and may provide received data for emergency rescue. User terminal 90 may be a terminal installed in a medical institution, and may provide received data to a doctor.

Figure 2:
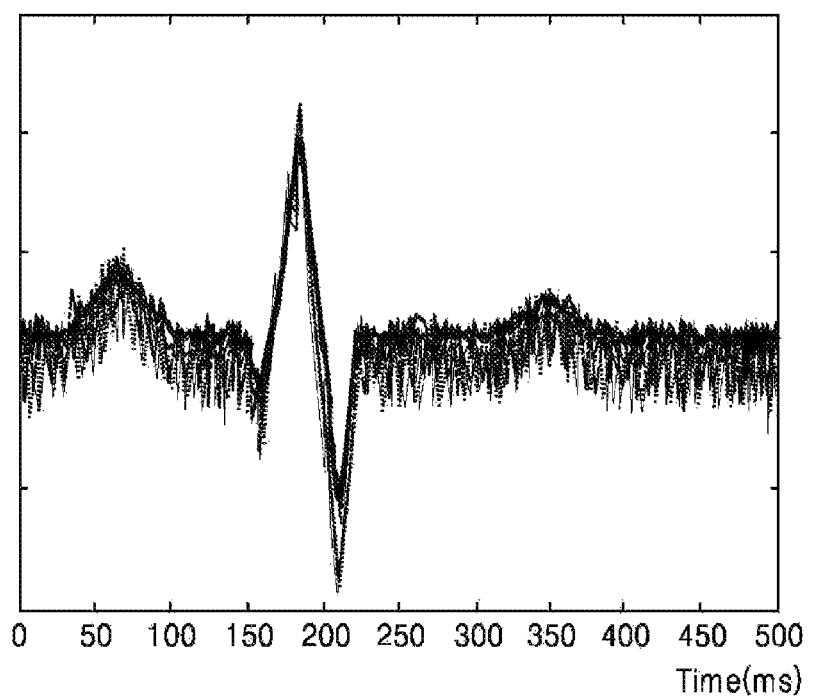
FIG. 2 is a graph in which electrocardiogram (ECG) signals sensed at different points in time overlap each other.

FIG. 2 is a graph in which ECGs sensed at different points in time overlap each other. As shown in FIG. 2, the ECG may include noise, but may have substantially the same form. Namely, the ECG may be signals that are generally repeated in a similar form.

The monitoring of a biomedical signal may enable a diagnosis of a body (for example, the body 10 of FIG. 1) by providing information about an anomaly occurring in a biomedical signal as well as a long-term change of the biomedical signal. According to an embodiment, an expected range of values of a sensed biomedical signal (e.g., an ECG sensed by sensor 12) may be set in advance and each of sensors 11 to 14 of FIG. 1 may periodically transmit statistical information of the sensed signal via a wireless channel and transmit only data, which corresponds to a signal that is out of a previously set range, via the wireless channel. Thus, the amount of data that is transmitted via the wireless channel may be reduced, and the battery life of one or all of sensors 11-14 may be extended.

Although FIG. 2 illustrates only ECG signals, biomedical signals other than an ECG may also have characteristics that are repeated in a similar form, and the inventive concept may also be applied to the monitoring of biomedical signals other than the ECG signals.

Figure 3:
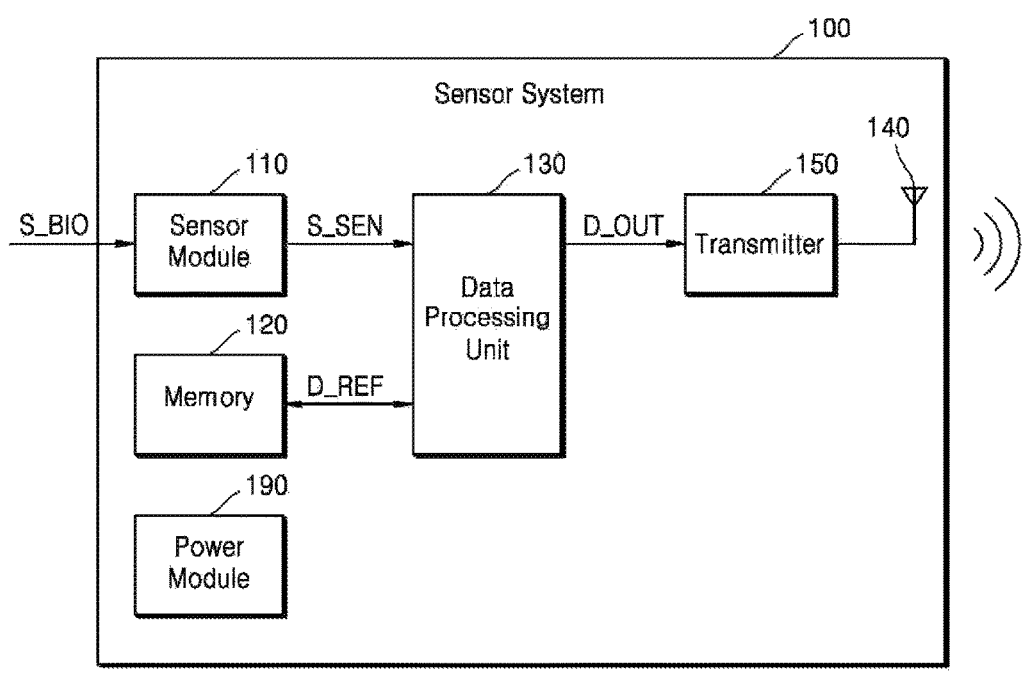
FIG. 3 is a block diagram of a sensor system according to an embodiment.

FIG. 3 is a block diagram of an example embodiment of a sensor system. In particular, FIG. 3 is a block diagram of a sensor system 100 which may be one embodiment of any of sensors 11-14 shown in FIG. 1. In that case, as described above with reference to FIG. 1, sensor system 100 of FIG. 3 may be attached to or implanted in the body 10 of FIG. 1 and may sense a biomedical signal generated in the body 10 and transmit data corresponding to the sensed biomedical signal via a wireless channel. As shown in FIG. 3, sensor system 100 may include a sensor module 110, a memory 120, a data processing unit 130, an antenna 140, a transmitter 150, and a power module 190.

Sensor module 110 may receive a biomedical signal S_BIO and output an electrical signal S_SEN. For example, sensor module 110 may sense an ECG corresponding to the biomedical signal S_BIO, and may convert the sensed ECG into an electrical analog signal and output the electrical analog signal. Sensor module 110 may continuously sense the biomedical signal S_BIO while sensor system 100 operates, and thus may generate a continuous electrical signal S_SEN. As shown in FIG. 3, the electrical signal S_SEN may be transmitted to data processing unit 130.

Memory 120 may be accessed by data processing unit 130 and may store reference data D_REF. As will be described later with reference to FIGS. 6A to 6D, the reference data D_REF may be used to determine whether data (i.e., data D_IN of FIG. 5, discussed below) exhibits an anomaly corresponding to an anomaly in the biomedical signal S_BIO. Memory 120 may include a volatile memory device, such as dynamic random access memory (DRAM), static random access memory (SRAM), mobile DRAM, double data rate synchronous dynamic random access memory (DDR SDRAM), low power DDR (LPDDR) SDRAM, graphic DDR (GDDR) SDRAM, or Rambus dynamic random access memory (RDRAM), or may include a non-volatile memory device, such as electrically erasable programmable read only memory (EEPROM), a flash memory, phase change random access memory (PRAM), resistance random access memory (RRAM), nano floating gate memory (NFGM), polymer random access memory (PoRAM), magnetic random access memory (MRAM) or ferroelectric random access memory (FRAM).

Data processing unit 130 may generate input data (e.g., the data D_IN of FIG. 5, discussed below) from the electrical signal S_SEN, and may determine whether to transmit the input data via transmitter 150 as output data D_OUT, based on the input data and the reference data D_REF. By transmitting only the output data D_OUT, which is generated by data processing unit 130 via a wireless channel, instead of transmitting all of the data which are generated from the electrical signal S_SEN via the wireless channel, the power consumption of sensor system 100 may be reduced. Sensor system 100 including data processing unit 130 may be referred to as a smart sensor. Details of data processing unit 130 will be described later with reference to FIG. 5.

Transmitter 150 may be connected to antenna 140 and may transmit the output data D_OUT, which is received from data processing unit 130, via a wireless channel, for example, Bluetooth, ZigBee, Wi-Fi or the like. As described above, transmitter 150 may consume relatively a lot of power while data transmission is performed via the wireless channel, and relatively less power when no data transmission is being performed.

Power module 190 may supply power to elements of sensor system 100, and may include a battery that outputs the power. While sensor system 100 operates, that is, senses the biomedical signal S_BIO and transmits the output data D_OUT via the wireless channel, power module 190 may supply power to sensor module 110, memory 120, data processing unit 130, and transmitter 150. The battery of power module 190 may be charged before sensor system 100 is attached to or implanted in a body (e.g., the body 10 of FIG. 1).

Figure 4:
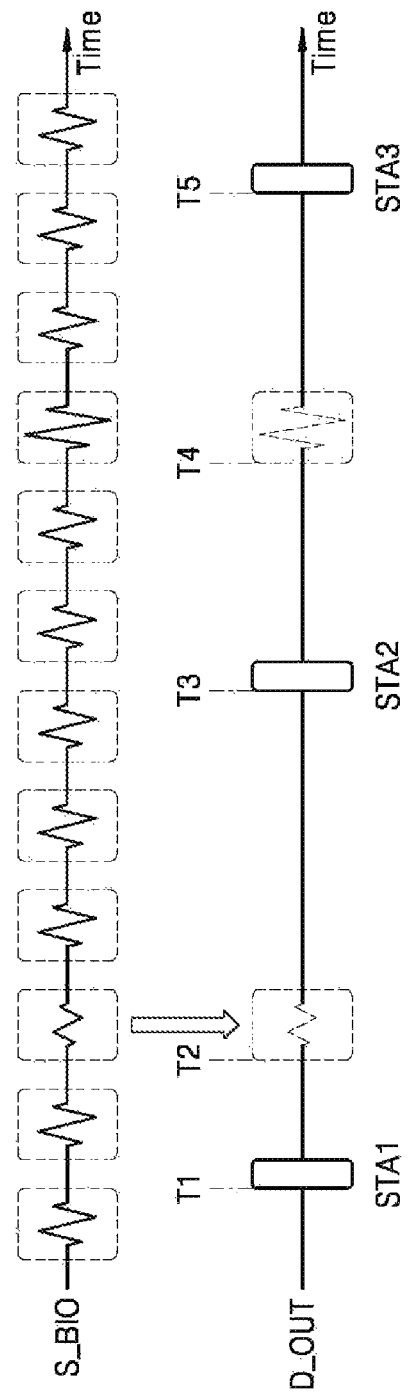
FIG. 4 is a diagram illustrating an example of an operation in which output data is generated by the sensor system of FIG. 3 from a biomedical signal.

FIG. 4 is a diagram illustrating an example of an operation in which the output data D_OUT is generated by sensor system 100 of FIG. 3 from the biomedical signal S_BIO. As described above with reference to FIG. 3, sensor system 100 of FIG. 3 may transmit only the output data D_OUT, which is generated by data processing unit 130 via the wireless channel, instead of transmitting of the data which are generated from the biomedical signal S_BIO (or the electrical signal S_SEN generated from the biomedical signal S_BIO) via the wireless channel, and thus, the power consumption of sensor system 100 may be reduced. Hereinafter, FIG. 4 will be described with reference to FIG. 3.

Referring to FIG. 4, the biomedical signal S_BIO may be repeated in a similar form over time, and the output data D_OUT may include pieces of statistical data STA1, STA2, and STA3, which are periodically generated. As described above with reference to FIG. 2, the biomedical signal S_BIO may be generally repeated in a similar form. Accordingly, data processing unit 130 may periodically output statistical data of the biomedical signal S_BIO. According to an embodiment, the statistical data STA1, STA2, and STA3 may be periodically generated as the output data D_OUT. In other words, a time interval between a time T1 when statistical data STA1 is generated and a time T3 when statistical data STA2 is generated may be substantially equal to that between the time T3 and a time T5 when statistical data STA3 is generated.

When a biomedical signal S_BIO having a form that is different from that of a general or expected biomedical signal occurs, data corresponding to the biomedical signal S_BIO may be generated as the output data D_OUT. For example, as shown in FIG. 4, when a biomedical signal S_BIO having an amplitude that is less than that of the general biomedical signal occurs, data corresponding to the biomedical signal S_BIO may be generated at a time T2 as the output data D_OUT. In addition, when a biomedical signal S_BIO having an amplitude that is greater than that of the general biomedical signal occurs, data corresponding to the biomedical signal S_BIO may be generated at a time T4 as the output data D_OUT.

Whether an anomaly has occurred in a biomedical signal S_BIO may be determined by sensor system 100, and only a biomedical signal S_BIO (or data corresponding to the biomedical signal S_BIO) of a period in which an anomaly has occurred may be transmitted via the wireless channel, and thus, the amount of data that is transmitted via the wireless channel from sensor system 100 may be remarkably reduced. In addition, sensor system 100 may also enable the long-term monitoring of the biomedical signal S_BIO by periodically transmitting the statistical data STA1, STA2, and STA3 of the biomedical signal S_BIO via the wireless channel.

Figure 5:
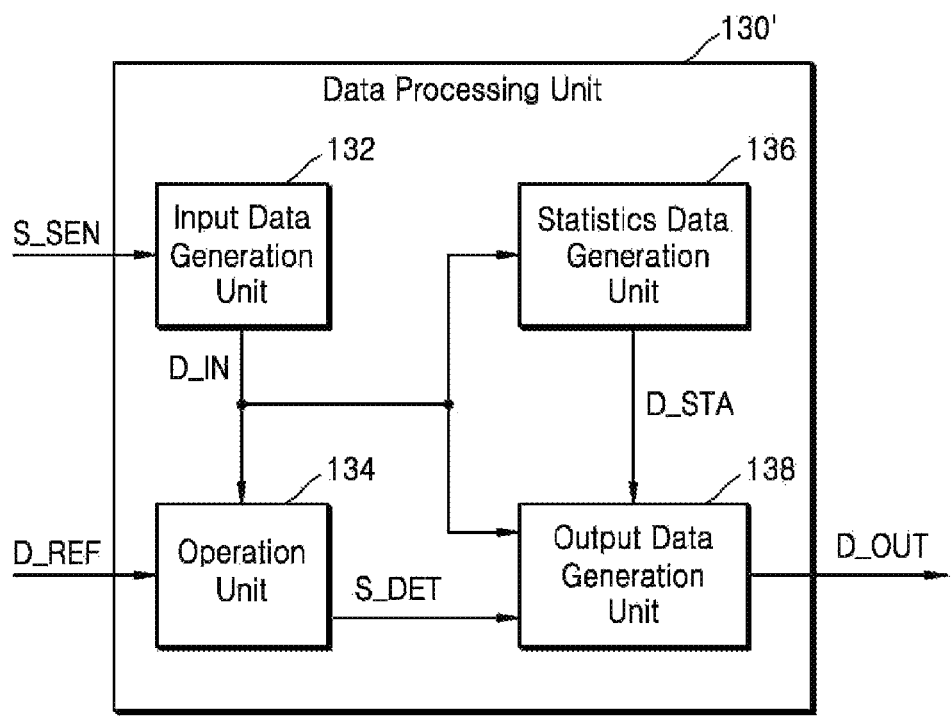
FIG. 5 is a block diagram illustrating an example embodiment of a data processing unit of FIG. 3.

FIG. 5 is a block diagram of a data processing unit 130', which is an example embodiment of data processing unit 130 of FIG. 3. As described above with reference to FIG. 3, data processing unit 130 of FIG. 3 may receive the electrical signal S_SEN from sensor module 110, receive the reference data D_REF from memory 120, and generate the output data D_OUT.

As shown in FIG. 5, data processing unit 130' may include an input data generation unit 132, an operation unit 134, a statistics data generation unit 136, and an output data generation unit 138. Each of input data generation unit 132, operation unit 134, statistics data generation unit 136, and output data generation unit 138 may be a hardware module, such as a hardware logic block or a processor, or may be a software module including a plurality of commands stored in a data storage medium and executed by a microprocessor. When at least one selected from input data generation unit 132, operation unit 134, statistics data generation unit 136, and output data generation unit 138 is a software module including a plurality of commands, data processing unit 130' may include the data storage medium (e.g., memory device) storing the plurality of commands and the processor that may execute the plurality of commands stored in the data storage medium (e.g., memory device).

Input data generation unit 132 may receive the electrical signal S_SEN and may generate input data D_IN from the electrical signal S_SEN. In other words, input data generation unit 132 may generate input data D_IN by pre-processing and segmenting the electrical signal S_SEN. For example, the biomedical signal S_BIO may include noise, as described above with reference to FIG. 2, and input data generation unit 132 may remove or reduce the noise by pre-processing the electrical signal S_SEN generated from the biomedical signal S_BIO. To monitor the biomedical signal S_BIO that is repeated in a similar form, data processing unit 132 may generate the input data D_IN by segmenting the electrical signal S_SEN generated from the biomedical signal S_BIO into sections corresponding to a repeating period. Each of the sections obtained by segmenting the electrical signal S_SEN may be referred to as a window. Input data generation unit 132 may generate the input data D_IN including a plurality of samples in the window. Details of an embodiment of input data generation unit 132 will be described later with reference to FIG. 6.

Operation unit 134 may receive the input data D_IN from input data generation unit 132, and receive the reference data D_REF from memory 120 of FIG. 3, and output a determination signal S_DET in response to D_IN and D_REF. Operation unit 134 may perform an operation on the input data D_IN and the reference data D_REF as operands to determine whether an anomaly has occurred in the input data D_IN and may output an activated determination signal S_DET when it is determined that an anomaly has occurred in the input data D_IN. As will be described later with reference to FIGS. 8A to 8C, operation unit 134 may determine whether an anomaly has occurred in the input data D_IN, through a relatively simple operation, and the input data D_IN, in which an anomaly has occurred, may be transmitted by operation unit 134 as the output data D_OUT via a wireless channel.

Statistics data generation unit 136 may receive the input data D_IN and in response thereto may output statistical data D_STA. Statistics data generation unit 136 may generate statistical data D_STA of the biomedical signal S_BIO, based on the input data D_IN. For example, statistics data generation unit 136 may calculate an average value, a maximum amplitude, a positive pulse width, and a negative pulse width of the input data D_IN, and may generate statistical data D_STA including the calculated numerical values. Statistical data D_STA of the input data D_IN corresponding to a plurality of windows may be accumulated (or stored), and accumulated statistical data D_STA may be periodically transmitted as the output data D_OUT via the wireless channel. In addition, as will be described later with reference to FIGS. 12A-12C, the statistical data D_STA may be used to generate the reference data D_REF.

Output data generation unit 138 may receive the input data D_IN, the statistical data D_STA, and the determination signal S_DET and in response thereto may output the output data D_OUT. Output data generation unit 138 may generate the output data D_OUT from the input data D_IN in response to an activated determination signal S_DET received from operation unit 134. For example, output data generation unit 138 may match a time stamp to the plurality of samples of the input data D_IN and may generate the output data D_OUT including the input data D_IN and the time stamp. The time stamp is information indicating a time period for which a biomedical signal S_SEN corresponding to the plurality of samples of the input signal S_SEN has been sensed and may be used to analyze the body 10 of FIG. 1 from the biomedical signal S_SEN.

According to an exemplary embodiment, output data generation unit 138 may generate output data D_OUT including the input data D_IN just as the input data D_IN is, or may generate output data D_OUT including data generated by processing the input data D_IN. For example, as illustrated in FIG. 8B, when the reference data D_REF includes average values of the samples of the input data D_IN, output data generation unit 138 may generate output data D_OUT including the samples of the input data D_IN and deviations from the average values. Thus, the size of the output data D_OUT may decrease.

Also, the output data generation unit 138 may generate the output data D_OUT from the statistical data D_STA during a predetermined period. For example, output data generation unit 138 may periodically generate output data D_OUT including an average value and maximum amplitude of the input data D_IN. As the statistical data D_STA of the input data D_IN is periodically transmitted as the output data D_OUT, the biomedical signal S_BIO may be efficiently monitored.

Figure 6:
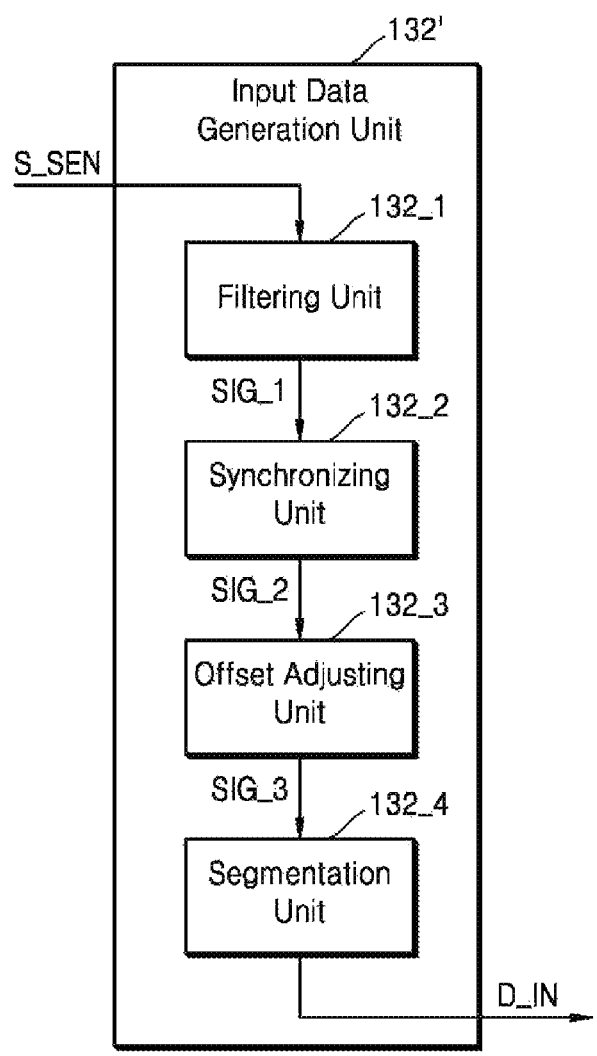
FIG. 6 is a block diagram illustrating an example embodiment of an input data generation unit of FIG. 5.

FIG. 6 is a block diagram of an input data generation unit 132', which is an example embodiment of input data generation unit 132 of FIG. 5. As described above with reference to FIG. 5, input data generation unit 132 may generate the input data D_IN by pre-processing and segmenting the electrical signal S_SEN. As shown in FIG. 6, input data generation unit 132' may include a filtering unit 132_1, a synchronizing unit 132_2, an offset adjusting unit 132_3, and a segmentation unit 132_4. Each of filtering unit 132_1, synchronizing unit 132_2, offset adjusting unit 132_3, and segmentation unit 132_4 may be a hardware module or a software module.

Filtering unit 132_1 may remove from the electrical signal S_SEN all of part of noise or a frequency component unnecessary for monitoring the electrical signal S_SEN by filtering the electrical signal S_SEN. When the electrical signal S_SEN is an analog signal, filtering unit 132_1 may be a filter circuit including a passive device and/or an active device, and a pass band of the filter circuit may be determined based on characteristics of a corresponding biomedical signal S_BIO.

Synchronizing unit 132_2 may synchronize an output signal SIG_1 of filtering unit 132_1 to the reference data D_REF. In order for operation unit 134 of FIG. 5 to operate on the input data D_IN and the reference data D_REF, samples included in the input data D_IN and samples included in the reference data D_REF may be synchronized by the synchronizing unit 132_2. For example, synchronizing unit 132_2 may extract a feature from the output signal SIG_1 of filtering unit 132_1 and may adjust a phase of a clock signal for sampling the output signal SIG_1, based on the extracted feature. The output signal SIG_1 may be sampled by using the clock signal having an adjusted phase, and thus, an output signal SIG_2 of synchronizing unit 132_2 may include a plurality of samples synchronized with the samples of the reference data D_REF. Each of the plurality of samples has a digital value.

Offset adjusting unit 132_3 may adjust an offset of the output signal SIG_2 of the synchronizing unit 132_2. The electrical signal S_SEN may have an offset that is variable depending on a state of the body 10 of FIG. 1. For example, an offset of the electrical signal S_SEN in a period in which the body 10 inhales may be different from that of the electrical signal S_SEN in a period in which the body 10 exhales. As the offset of the electrical signal S_SEN is adjusted by offset adjusting unit 132_3, it is possible to prevent operation unit 134 of FIG. 5 from erroneously determining that an anomaly exists in the input data D_IN as a result of the different offsets.

Segmentation unit 132_4 may generate the input data D_IN by segmenting an output signal SIG_3 of offset adjusting unit 132_3. In other words, segmentation unit 132_4 may segment output signal SIG_3 based on a window, and thus, input data D_IN including a plurality of samples may be formed in the window.

FIGS. 7A to 7D are diagrams illustrating examples of the input data D_IN and the reference data D_REF which may be employed in data processing unit 130' of FIG. 5. As described above with reference to FIG. 5, operation unit 134 of FIG. 5 may detect whether the input data D_IN exhibits or includes an anomaly, based on the input data D_IN and the reference data D_REF. Details of an example of operation unit 134 performing an operation on the input data D_IN and the reference data D_REF will be described below with reference to FIGS. 8A to 8C.

In the examples of FIGS. 7A to 7D, the reference data D_REF may define an upper limit of the input data D_IN and a lower limit of the input data D_IN. The reference data D_REF may include a series of samples (i.e., reference samples), and each of the series of samples may correspond to a series of samples (i.e., input samples) of the input data D_IN over a given time period of the biomedical signal S_BIO. Each of the reference samples may include an upper limit and a lower limit of a corresponding input sample, and whether a value of the corresponding input sample is out of range between the upper limit and the lower limit may be determined by operation unit 134.

Figure 7A:
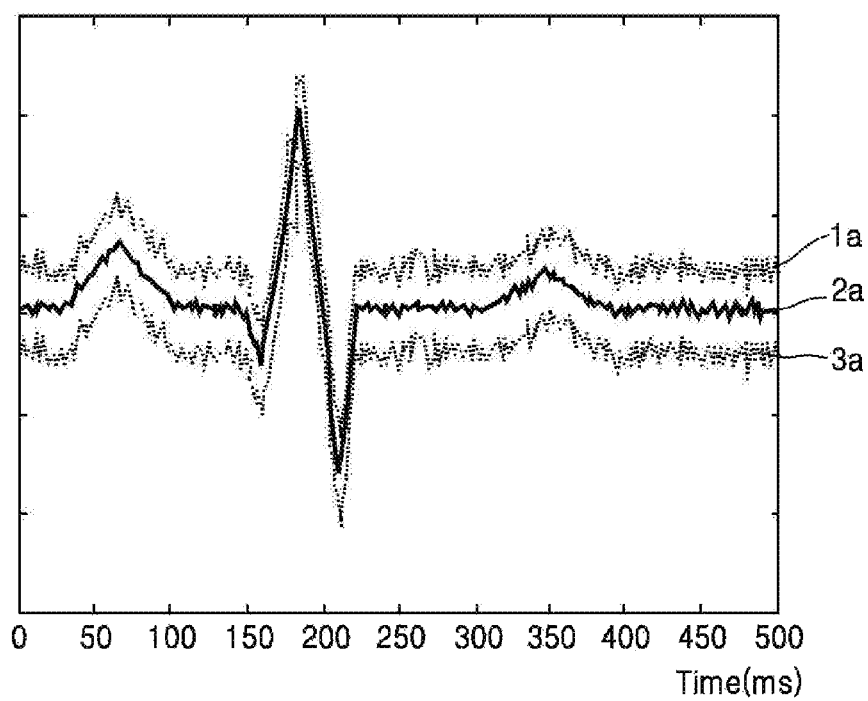
FIGS. 7A, 7B, 7C and 7D are diagrams illustrating examples of input data and reference data which may be employed in the embodiment of a data processing unit illustrated in of FIG. 5.

FIG. 7A illustrates reference data D_REF and input data D_IN which exhibits or includes an anomaly. For convenience of illustration, input samples 2a of the input data D_IN are illustrated as a value obtained by averaging input samples of the input data D_IN which correspond to 20 windows. Referring to FIG. 7A, reference samples of the reference data D_REF may define an upper limit 1a and a lower limit 3a, and input samples 2a of the input data D_IN may have values between upper limit 1a and lower limit 3a of the reference samples. For example, upper limit 1a and lower limit 3a may be +/−3 sigma ($\sigma$) (standard deviation) values of input samples of the input data D_IN which correspond to a plurality of windows.

Figure 7B:
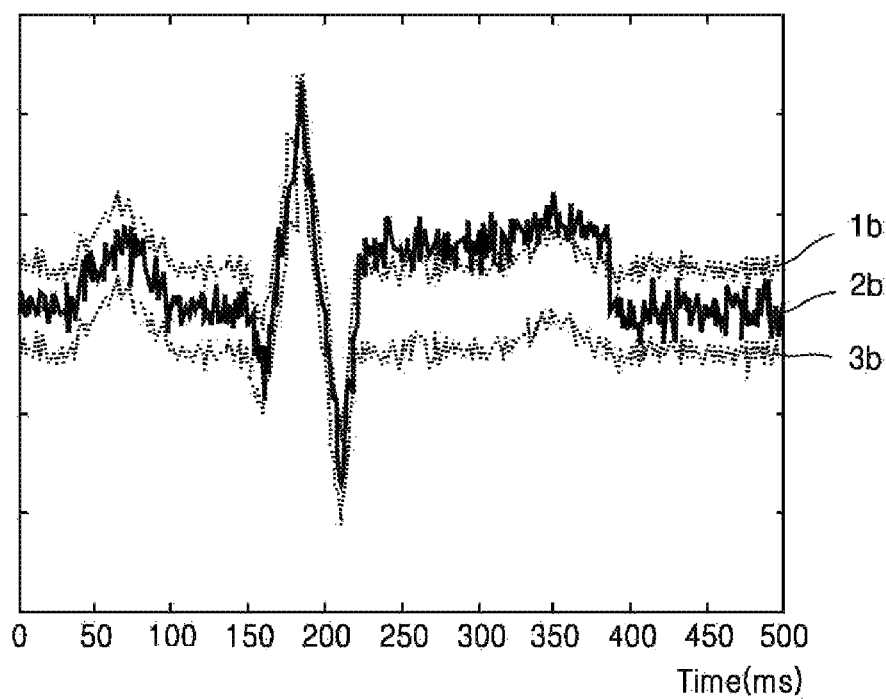

FIG. 7B illustrates reference data D_REF and input data D_IN, which exhibits or includes an anomaly. As shown in FIG. 7B, the input data D_IN may include input samples having a value exceeding an upper limit 1b of the reference data D_REF in a period from about 220 ms to about 370 ms. Accordingly, operation unit 134 of FIG. 5 may determine that an anomaly has occurred in input data D_IN including input samples 2b shown in FIG. 7B, and may output an activated determination signal S_DET.

Figure 7C:
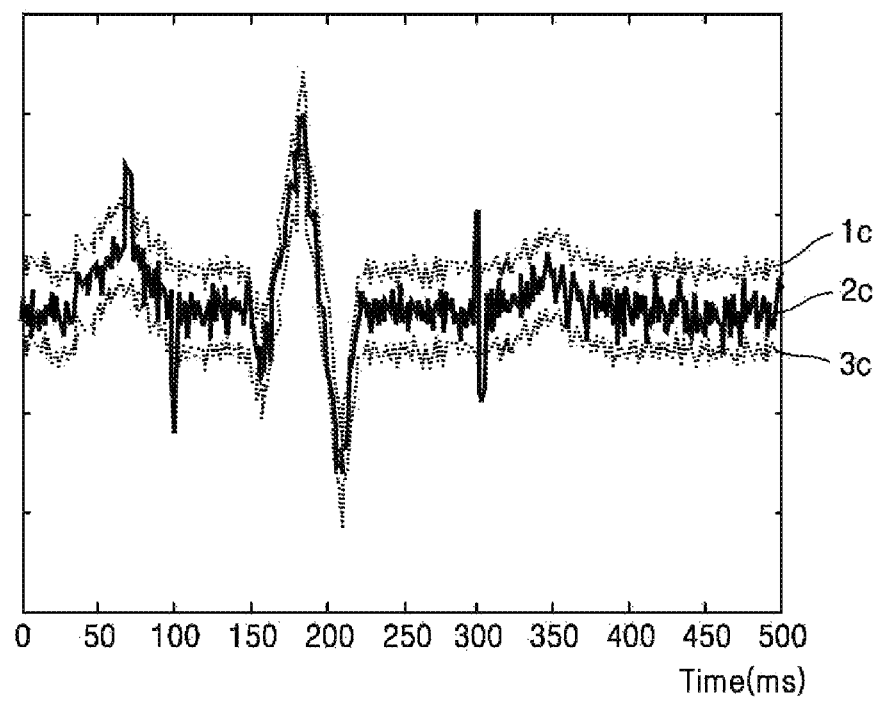

FIG. 7C illustrates reference data D_REF and input data D_IN including noise. Although input data D_IN pre-processed by input data generation unit 132 of FIG. 5 is generated, the input data D_IN may include noise that does not occur from a biomedical signal S_BIO. As shown in FIG. 7C, the input data D_IN may include input samples that are out of range between an upper limit 1c and a lower limit 3c of the reference data D_REF at about 70 ms, about 100 ms, and about 300 ms. To prevent determining that an anomaly has occurred in input data D_IN including input samples 2c shown in FIG. 7C, operation unit 134 may count the number of input samples of the input data D_IN which are out of range between upper limit 1c and lower limit 3c and may determine that an anomaly has occurred in the input data D_IN, if the counted number of input samples exceeds a predetermined threshold number.

Figure 7D:
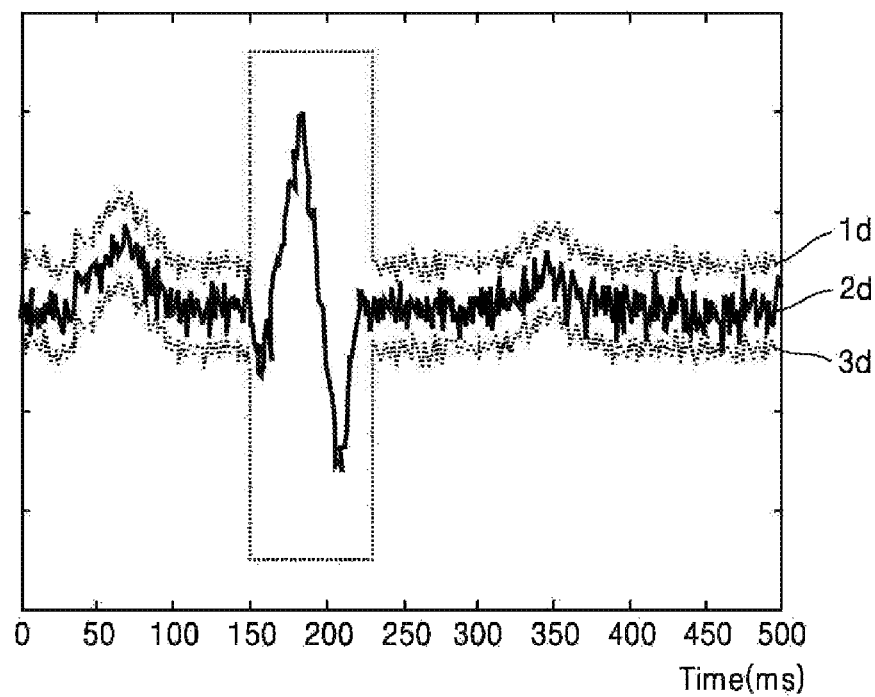

Operation unit 134 may give a low weight to a section of the input data D_IN in which noise frequently occurs or a section of input data D_IN which is not important for monitoring the biomedical signal S_BIO. For example, FIG. 7D illustrates input data D_IN and reference data D_REF including upper and lower limits having constant values in a specific section. In a section of the input data D_IN in which noise frequently occurs or a section of input data D_IN which is not important for monitoring a biomedical signal S_BIO, each reference sample of the reference data D_REF may include an upper limit and a lower limit, which have a relatively large difference therebetween. As shown in FIG. 7D, in a section from about 150 ms to about 230 ms, an upper limit 1d or a lower limit 3d may have a constant value and provide a relatively larger margin than in another section to input samples 2d of the input data D_IN.

Figure 8A:
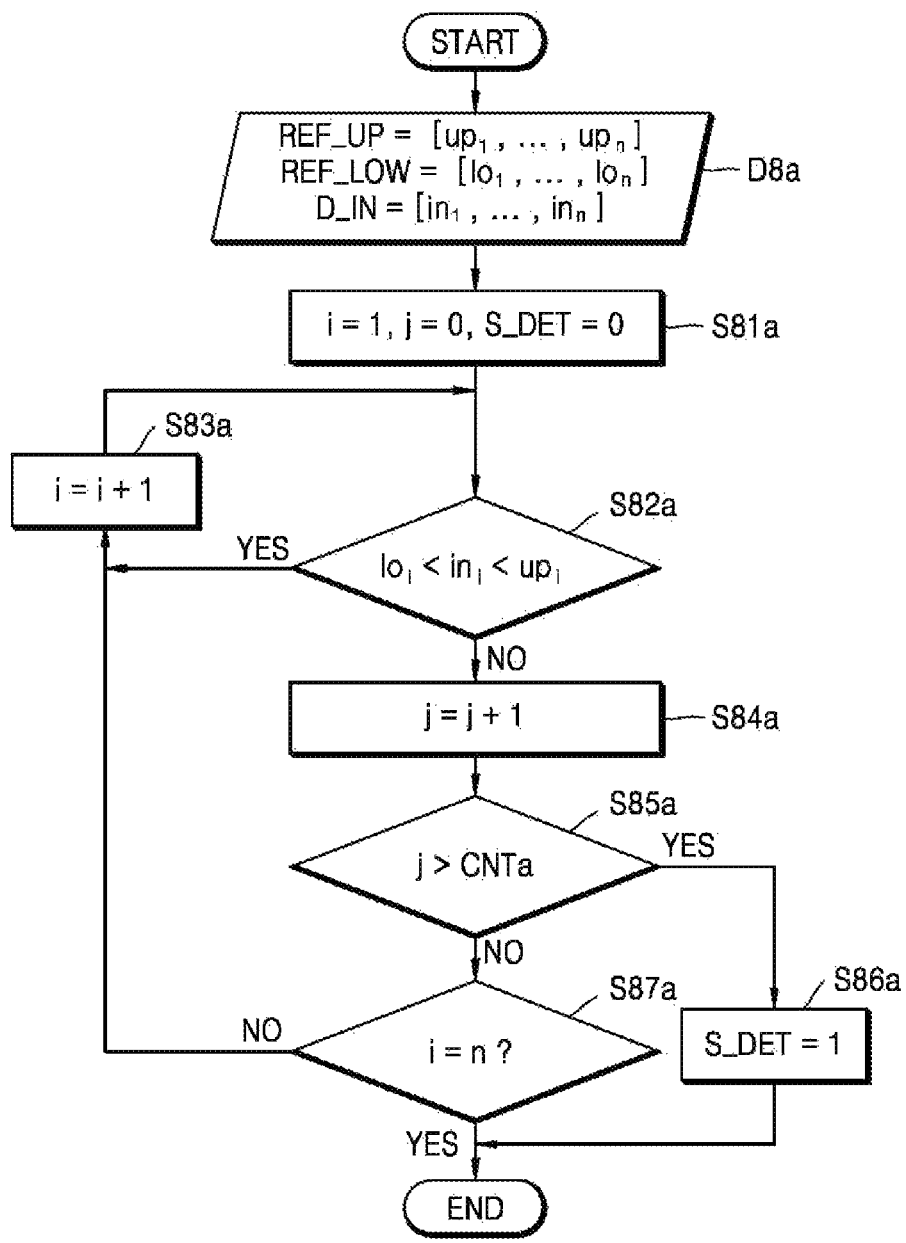
FIGS. 8A, 8B and 8C are flowcharts illustrating example operations of an embodiment of an operation unit of FIG. 5.
Figure 8B:
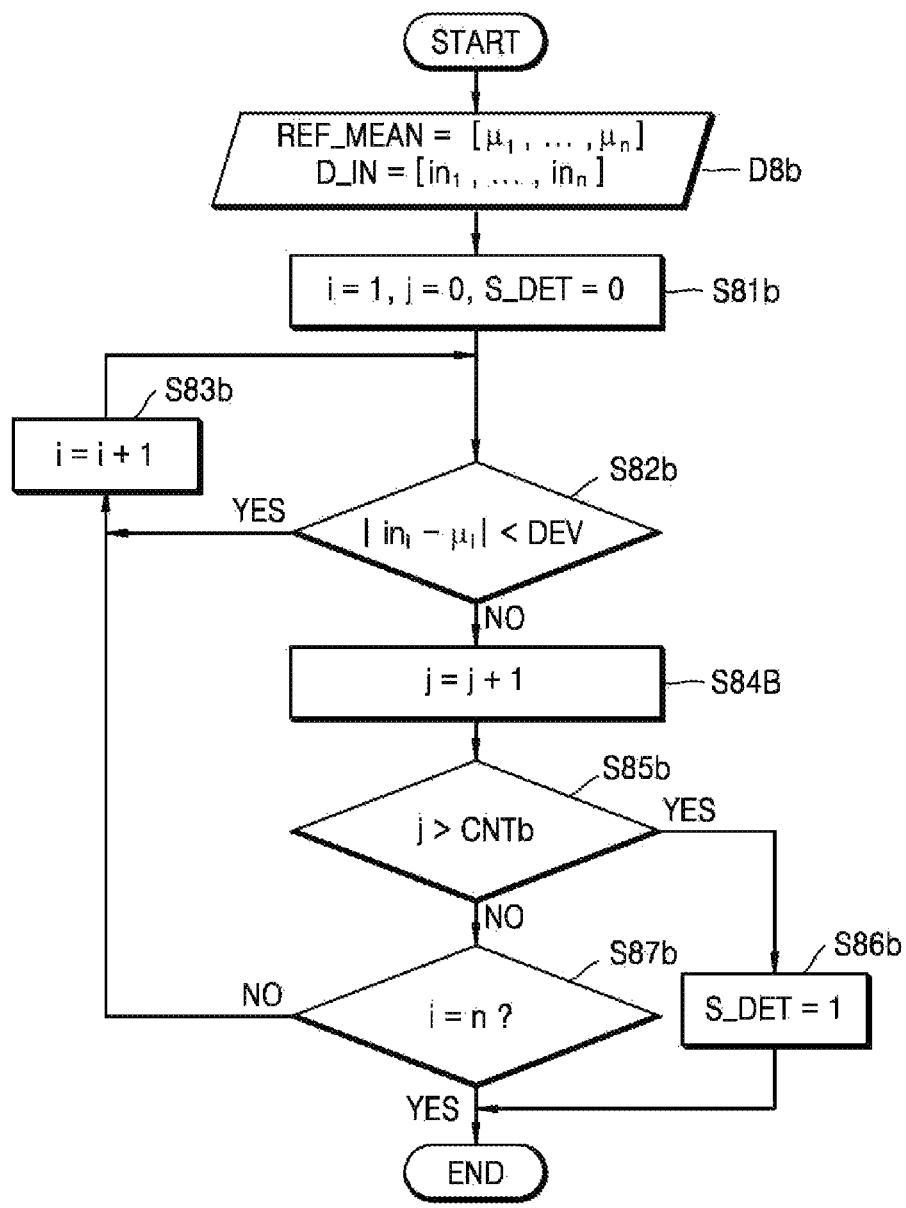
Figure 8C:
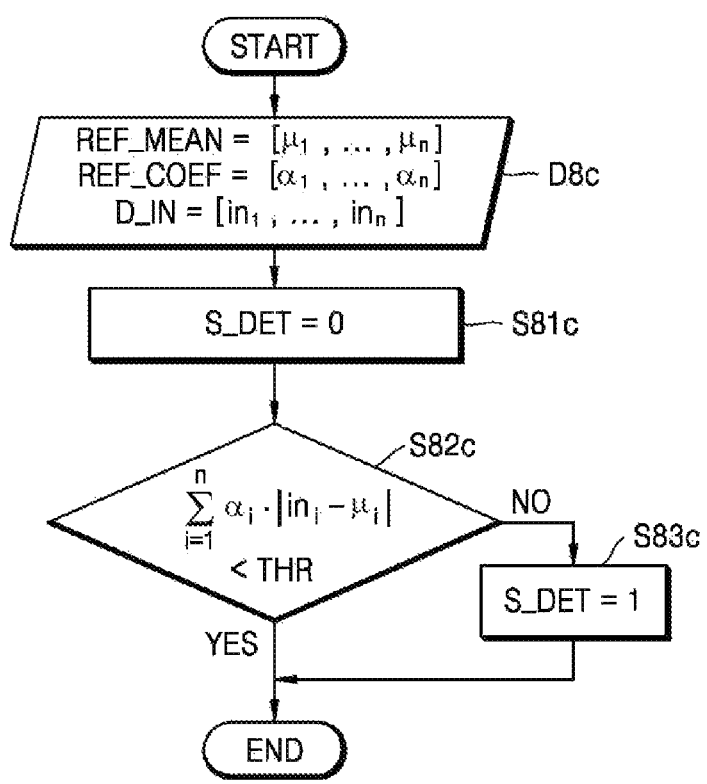

FIGS. 8A to 8C are flowcharts illustrating example operations of operation unit 134 of FIG. 5. As described above with reference to FIG. 5, operation unit 134 may determine whether an anomaly has occurred in input data D_IN based on the input data D_IN and reference data D_REF, and may output an activated determination signal S_DET when it is determined that an anomaly has occurred in the input data D_IN. In FIGS. 8A to 8C, it is assumed that the activated determination signal S_DET has a value of '1'. FIGS. 8A to 8C will be described with reference to FIG. 5, and descriptions of FIGS. 8B and 8C, which are the same as descriptions of FIG. 8A, will be omitted.

Referring to FIG. 8A, operation unit 134 may receive data D8a corresponding to a given time period of the sensed biomedical signal S_BIO. As shown in FIG. 8A, the data D8a may include upper limit data REF_UP and lower limit data REF_LOW as reference data D_REF, and may also include input data D_IN. The upper limit data REF_UP may include a series of upper limits $up_1, \ldots,$ and $up_n$, corresponding to a plurality of maximum expected values of the sensed biomedical signal S_BIO, the lower limit data REF_LOW may include a series of lower limits $lo_1, \ldots, lo_n$, corresponding to a plurality of minimum expected values of the sensed biomedical signal S_BIO, and a pair including an upper limit and a lower limit corresponding thereto (e.g., the upper limit $up_1$ and the lower limit $lo_1$) may form one reference sample. The input data D_IN may include a series of input samples $in_1, \ldots,$ and $in_n$. According to embodiments, each of the series of upper limits $up_1, \ldots,$ and $up_n$ may be a positive multiple (e.g., $+3\sigma$) of $\sigma$ of an input sample corresponding thereto. In addition, as shown in FIG. 7D, the upper limit data REF_UP may include successive upper limits having the same value. Similarly, each of the series of lower limits $lo_1, \ldots,$ and $lo_n$, corresponding to a plurality of minimum expected values of the sensed biomedical signal S_BIO, may be a negative multiple (e.g., $-3\sigma$) of $\sigma$ of an input sample corresponding thereto, and the lower limit data REF_LOW may include successive lower limits having the same value.

In operation S81a, operation unit 134 may initialize variables and signals. A variable 'i' is a variable increasing from 1 to n (where n is an integer that is equal to or greater than 2) and may be used to sequentially select a series of reference samples and a series of input samples. A variable 'j' may be used to count the number of input samples that are out of the range between an upper limit and a lower limit and may be set to '0' in operation S81a. In addition, the determination signal S_DET may be set to '0' and thus be deactivated.

In operation S82a, operation unit 134 may determine whether an input sample $in_i$ is between an upper limit $up_i$ defining a maximum expected value of the input sample $in_i$, and a lower limit $lo_i$ defining a minimum expected value if the input sample $in_i$. If it is determined that the input sample $in_i$ is between the upper limit $up_i$ and the lower limit $lo_i$, the operation unit 134 may increase the variable 'i' by '1' to start an operation with respect to a next input sample and a reference sample (operation S83a). Otherwise, if it is determined that the input sample $in_i$ is out of range between the upper limit $up_i$ and the lower limit $lo_i$, the operation unit 134 may increase the variable 'j' by '1' to count the number of input samples that are out of range between an upper limit and a lower limit (operation S84a).

In operation S85a, operation unit 134 may compare the variable 'j' with 'CNTa' to determine whether the number of input samples that are out of range between the upper limit and the lower limit exceeds a predetermined number. In an embodiment, the 'CNTa' may be '0', and thus in that embodiment when any input sample is out of range between the upper limit and the lower limit, it may be determined that an anomaly has occurred in the input data D_IN.

If it is determined that the number of input samples that are out of range between the upper limit and the lower limit exceeds the predetermined number, then operation unit 134 may set the determination signal S_DET to '1' to activate the determination signal S_DET (operation S86a), and then may end an operation on the input data D_IN. Otherwise, if it is determined that the number of input samples that are out of range between the upper limit and the lower limit does not exceed the predetermined number, then operation unit 134 may compare the variable 'i' with the variable 'n' to determine whether an operation on the last input sample $in_n$ has ended (operation S87a). If it is determined that the operation on the last input sample $in_n$ has not ended, operation unit 134 may increase the variable 'i' by '1' to start an operation with respect to a next input sample and a reference sample (operation S83a). If it is determined that the operation on the last input sample $in_n$ has ended, an operation on the input data D_IN may be ended and the determination signal S_DET may remain in a deactivated state (i.e., a state in which the determination signal S_DET has been set to '0').

Referring to FIG. 8B, operation unit 134 may receive data D8b corresponding to a given time period of the sensed biomedical signal S_BIO. As shown in FIG. 8B, the data D8b may include average data REF_MEAN as reference data D_REF. The average data REF_MEAN may include a series of average or mean values $\mu_1, \ldots,$ and $\mu_n$, and each of the averages $\mu_1, \ldots,$ and $\mu_n$ may form one reference sample. Operations S81b, S83b, S86b, and S87b of FIG. 8B may be the same as or similar to operations S81a, S83a, S86a, and S87a of FIG. 8A, respectively.

In operation S82b, operation unit 134 may compare a difference between an input sample $in_i$ and an average $\mu_i$ with a predetermined or defined deviation value DEV to determine whether the input sample $in_i$ is within a constant deviation, i.e., the predetermined deviation DEV, from the average $\mu_i$. That is, the magnitude of a difference between each input sample $in_i$ and the corresponding mean value $\mu_i$, is compared to the defined deviation value DEV to determine for each input sample $in_i$ whether the input sample $in_i$ indicates that the sensed biomedical signal falls inside or outside the expected range of values of the sensed biomedical signal. If it is determined that the input sample $in_i$ is within the constant deviation DEV from the average $\mu_i$, operation unit 134 may increase a variable 'i' by '1' to start an operation with respect to a next input sample and a reference sample (operation S83b). Otherwise, if it is determined that the input sample $in_i$ is not within the constant deviation DEV from the average $\mu_i$, operation unit 134 may increase a variable 'j' by '1' to increase the number of input samples that are not within a constant deviation from an average (operation S84b).

In operation S85b, operation unit 134 may compare the variable 'j' with 'CNTb' to determine whether the number of input samples that are not within the constant deviation from the average exceeds a predetermined number. In an embodiment, the 'CNTb' may be '0', and thus in that embodiment when any input sample is not within the constant deviation from the average, it may be determined that an anomaly has occurred in the input data D_IN.

Referring to FIG. 8C, operation unit 134 may receive data D8c corresponding to a given time period of the sensed biomedical signal S_BIO. As shown in FIG. 8C, the data D8c may include average data REF_MEAN and coefficient data REF_COEF as reference data D_REF. The average data REF_MEAN may include a series of averages $\mu_1, \ldots,$ and $\mu_n$, the coefficient data REF_COEF may include a series of weighting coefficients $\alpha_1, \ldots,$ and $\alpha_n$, and a pair including an average and a weighting coefficient corresponding thereto (e.g., the average $\mu_1$ and the coefficient $\alpha_1$) may form one reference sample.

In operation S81c, operation unit 134 may set a determination signal S_DET to '0' to initialize the determination signal S_DET.

In operation S82c, the operation unit 134 may calculate a weighted difference value $\alpha_i \cdot |in_i - \mu_i|$ by multiplying the weighting coefficient $\alpha_i$ and a magnitude of a difference between an input sample $in_i$ and an average or mean value $\mu_i$, and may determine whether the sum of the weighted difference values corresponding to a plurality of input samples corresponding to a given time period of the sensed biomedical signal S_BIO is less than a predetermined value THR. As described above with reference to FIGS. 7C and 7D, the input data D_IN may include a section in which noise frequently occurs or a section that is not important for monitoring a biomedical signal S_BIO. Coefficients corresponding to input samples included in these sections may have low values, and thus, whether an anomaly has occurred in input data D_IN may be more accurately determined. In addition, a coefficient may have a value (e.g., $1/(3\sigma)$) that is inversely proportional to a standard deviation, and thus, an influence, which is caused by input samples of a section in which a large deviation occurs, may be reduced.

Although FIG. 8C illustrates an example of calculating a sum corresponding to all input samples $in_1, \ldots,$ and $in_n$, operation unit 134 may calculate a sum corresponding to input samples included in a section that is important for determining whether an anomaly has occurred. In other words, operation unit 134 may compare a sum corresponding to less than n input samples to the predetermined value THR.

When the sum is less than the predetermined value THR, operation unit 134 may end an operation on the input data D_IN, and thus, the determination signal S_DET may remain in a deactivated state (i.e., a state in which the determination signal S_DET has been set to '0'). When the sum is not less than the predetermined value THR, operation unit 134 may set the determination signal S_DET to '1' to activate the determination signal S_DET (operation S83c), and then may end an operation on the input data D_IN.

Figure 9:
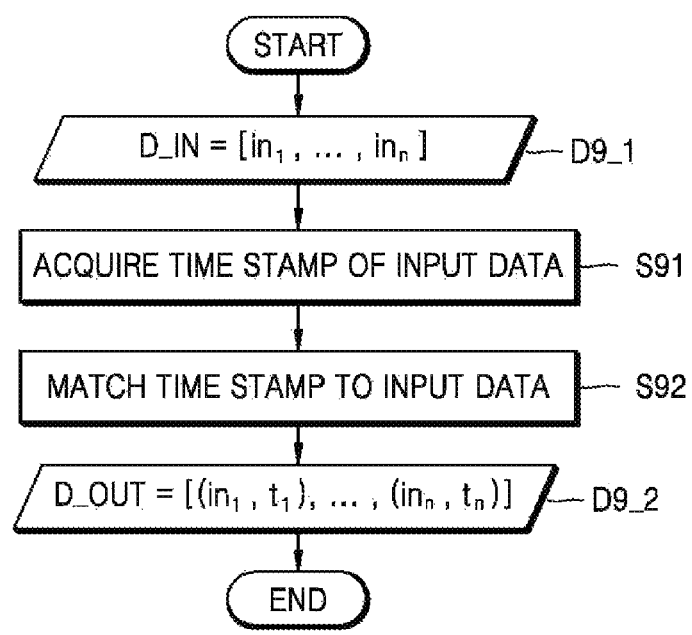
FIG. 9 is a flowchart illustrating an example operation of an embodiment of an output data generation unit of FIG. 5.

FIG. 9 is a flowchart illustrating an example operation of output data generation unit 138 of FIG. 5. As described above with reference to FIG. 5, output data generation unit 138 may generate output data D_OUT from input data D_IN when an activated determination signal S_DET is received. In the embodiment of FIG. 9, output data generation unit 138 may generate output data D_OUT by adding a time stamp to input data D_IN. Hereinafter, FIG. 9 will be described with reference to FIG. 5.

Referring to FIG. 9, output data generation unit 138 may receive data D9_1. As shown in FIG. 9, the data D9_1 may include input data D_IN including a series of input samples $in_1, \ldots,$ and $in_n$.

In operation S91, the output data generation unit 138 may include a time stamp of input data D_IN. For example, the output data generation unit 138 may receive time stamps of a series of input samples $in_1, \ldots,$ and $in_n$ of input data D_IN from synchronizing unit 132_2 of input data generation unit 132' of FIG. 6. For example, output data generation unit 138 may receive a time stamp of a first input sample $in_1$ and may generate time stamps corresponding to the remaining input samples $in_2, \ldots,$ and $in_n$, based on a sampling period.

In operation S92, output data generation unit 138 may match a time stamp to the input data D_IN. A series of time stamps may be obtained in operation S91, and data D9_2 may be generated by matching the series of time stamps to the input samples $in_1, \ldots,$ and $in_n$ of the input data D_IN in operation S92. As shown in FIG. 9, the data D9_2 may include data D_OUT including pairs $(in_1, t_1), \ldots,$ and $(in_n, t_n)$ including an input sample and a time stamp.

Figure 10:
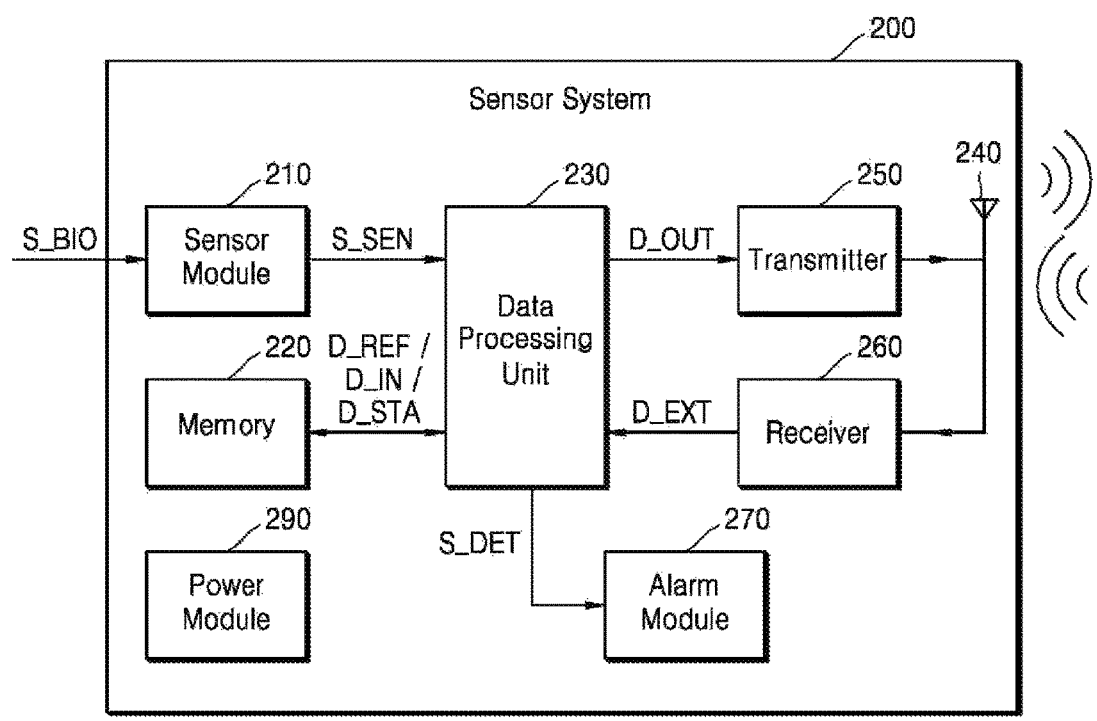
FIG. 10 is a block diagram of an example embodiment of a sensor system.

FIG. 10 is a block diagram of another embodiment of a sensor system. In particular, FIG. 10 is a block diagram of a sensor system 200 which may be another embodiment of any of sensors 11-14 shown in FIG. 1. In that case, similar to the sensor system 100 of FIG. 3, sensor system 200 may be attached to or implanted in the body 10 of FIG. 1 and may sense a biomedical signal generated in the body 10 and transmit data corresponding to the sensed biomedical signal via a wireless channel. Unlike sensor system 100 of FIG. 3, sensor system 200 may receive external data D_EXT via a wireless channel. As shown in FIG. 10, sensor system 200 may include a sensor module 210, a memory 220, a data processing unit 230, an antenna 240, a transmitter 250, a receiver 260, an alarm module 270, and a power module 290. Descriptions of FIG. 10 which are the same as descriptions of FIG. 3 will be omitted.

Memory 220 may be accessed by data processing unit 230, and may store reference data D_REF, input data D_IN, and statistical data D_STA. Referring to FIG. 10, together with FIG. 5, input data generated by an input data generation unit of data processing unit 230 may be stored in memory 220. For example, the input data D_IN or the statistical data D_STA, stored in memory 220, may be transmitted by the data processing unit 230 via the transmitter 250 as output data D_OUT, in response to a request included in the external data D_EXT received via the receiver 260. In addition, the statistics data generation unit of the data processing unit 230 may generate new statistical data from the input data D_IN or the statistical data D_STA, stored in memory 220.

Receiver 260 may be connected to antenna 240 and may communicate the external data D_EXT received via a wireless channel to data processing unit 230. As will be described later with reference to FIGS. 13 and 14A, the external data D_EXT may include reference data or biomedical data, and data processing unit 230 may use the reference data or biomedical data included in the external data D_EXT to prepare the reference data D_REF.

Alarm module 270 may output at least one selected from an image, light, vibration, and sound, in response to an activated determination signal S_DET received from data processing unit 230. When an anomaly occurs in input data D_IN, alarm module 270 may output a signal, which may be sensed from the outside of sensor system 200, to report that an anomaly has occurred in the input data D_IN. Accordingly, whether an anomaly has occurred in a biomedical signal S_BIO may be immediately checked on the spot.

According to an embodiment, alarm module 270 may be used for determining the location of sensor system 200. To sense a biomedical signal S_BIO occurring in the body 10 of FIG. 1, sensor system 200 needs to be attached to or implemented in a correct location on the body 10. The reference data D_REF may be set to determine the location of sensor system 200. In other words, data processing unit 230 may determine whether a biomedical signal S_BIO sensed based on input data D_IN generated from the biomedical signal S_BIO and the reference data D_REF is appropriate, and thus may output an activated determination signal S_DET. For example, the reference data D_REF may be set to have a relatively small margin while the location of sensor system 200 is determined. When the size of a received biomedical signal S_BIO is sufficiently large as the location of sensor system 200 moves, input data D_IN generated from the received biomedical signal S_BIO may be out of range that is defined by the reference data D_REF, and thus, an activated determination signal S_DET may be output. Alarm module 270 may output a signal to the outside of sensor system 200 in response to the activated determination signal S_DET, and may report that sensor system 200 is in a correct location.

Figure 11:
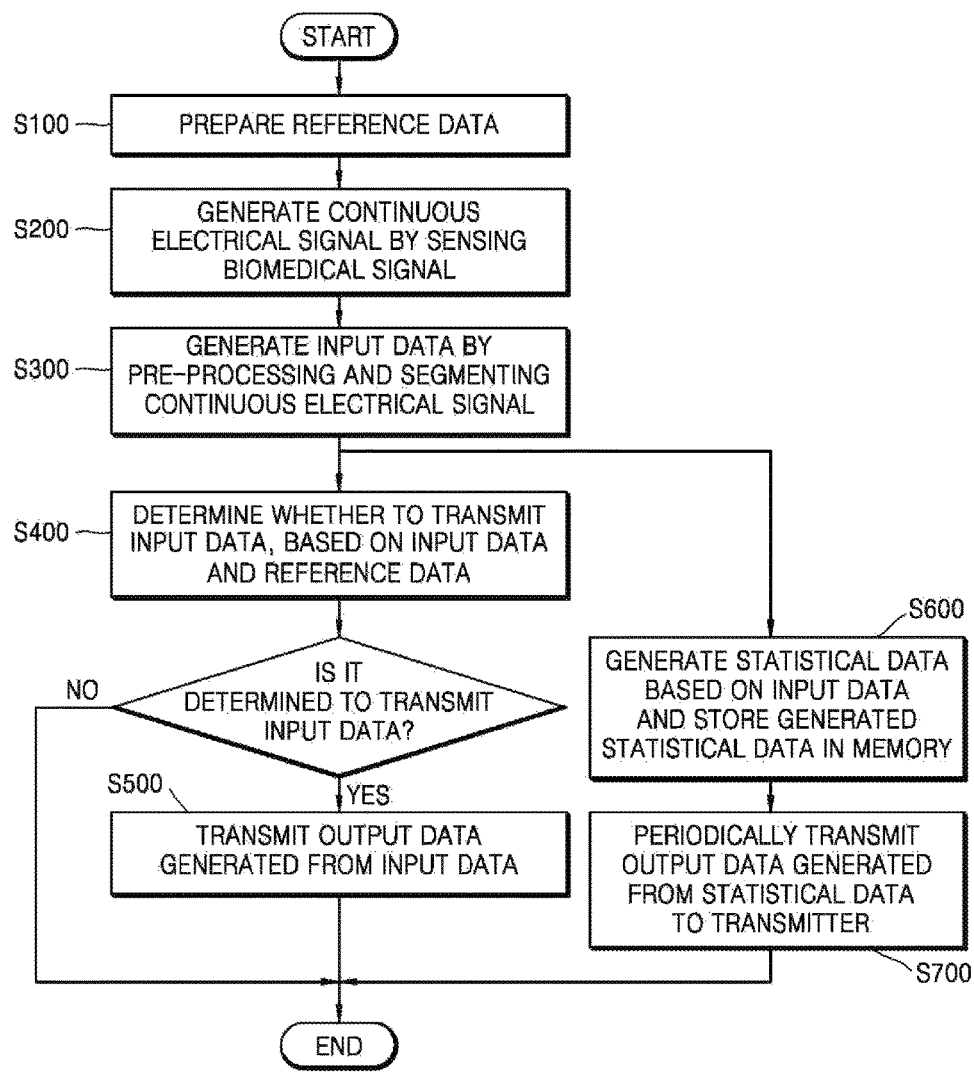
FIG. 11 is a flowchart illustrating an example embodiment of a method of monitoring a biomedical signal.

FIG. 11 is a flowchart illustrating an example embodiment of a method of monitoring a biomedical signal. Specifically, FIG. 11 is a flowchart showing a procedure for processing input data D_IN generated from a biomedical signal S_BIO. As shown in FIG. 11, the method of monitoring a biomedical signal may include a plurality of operations S100 to S700. Hereinafter, FIG. 11 will be described with reference to FIG. 10.

An operation S100 may include preparing reference data D_REF. The reference data D_REF is data that is used for determining whether an anomaly has occurred in input data D_IN. The reference data D_REF may be generated in sensor system 200 of FIG. 10 or may be received from the outside of sensor system 200. Operation S100 may be performed when the monitoring of a biomedical signal S_BIO is started or the monitoring of the biomedical signal S_BIO is ended, and operations S200 to S700 may be repeatedly performed. Details of embodiments of operation S100 will be described later with reference to FIGS. 12A to 12C.

An operation S200 may include generating a continuous electrical signal S_SEN by sensing the biomedical signal S_BIO. For example, sensor module 210 of FIG. 10 may continuously convert the biomedical signal S_BIO into an electrical signal S_SEN, and thus may generate the continuous electrical signal S_SEN.

An operation S300 may include generating input data D_IN by pre-processing and segmenting the continuous electrical signal S_SEN. For example, an input data generation unit included in data processing unit 230 of FIG. 10 may generate input data D_IN including a series of samples (or input samples) by pre-processing and segmenting the continuous electrical signal S_SEN.

An operation S400 may include determining whether to transmit the input data D_IN, based on the input data D_IN and the reference data D_REF. Instead of transmitting data corresponding to the entire biomedical signal S_BIO (or entire electrical signal S_SEN), an operation unit included in data processing unit 230 of FIG. 10 may determine whether an anomaly has occurred in the input data D_IN based on the reference data D_REF and the input data D_IN, and it may be determined to transmit input data, in which an anomaly has occurred, to an external device as output data D_OUT.

If it is determined to transmit input data to an external device, an operation of transmitting output data D_OUT generated from the input data D_IN may be performed in operation S500. For example, transmitter 250 of FIG. 10 may transmit output data D_OUT, received from data processing unit 230, via antenna 240.

When the input data D_IN is generated, in an operation statistical data D_STA may be generated based on the input data D_IN and the generated statistical data D_STA may be stored in a memory. For example, a statistics data generation unit included in data processing unit 230 of FIG. 10 may generate statistical data D_STA including statistical information of a biomedical signal S_BIO based on the input data D_IN, and may store the generated statistical data D_STA in memory 220 or transmit the generated statistical data D_STA to an output data generation unit of data processing unit 230.

An operation S700 may include periodically communicating output data D_OUT generated from the statistical data D_STA to a transmitter. For example, the output data generation unit included in data processing unit 230 of FIG. 10 may periodically generate output data D_OUT from received statistical data, and may communicate the generated output data D_OUT to transmitter 250. Accordingly, transmitter 250 may periodically transmit output data D_OUT including statistical data D_STA via a wireless channel.

Figure 12B:
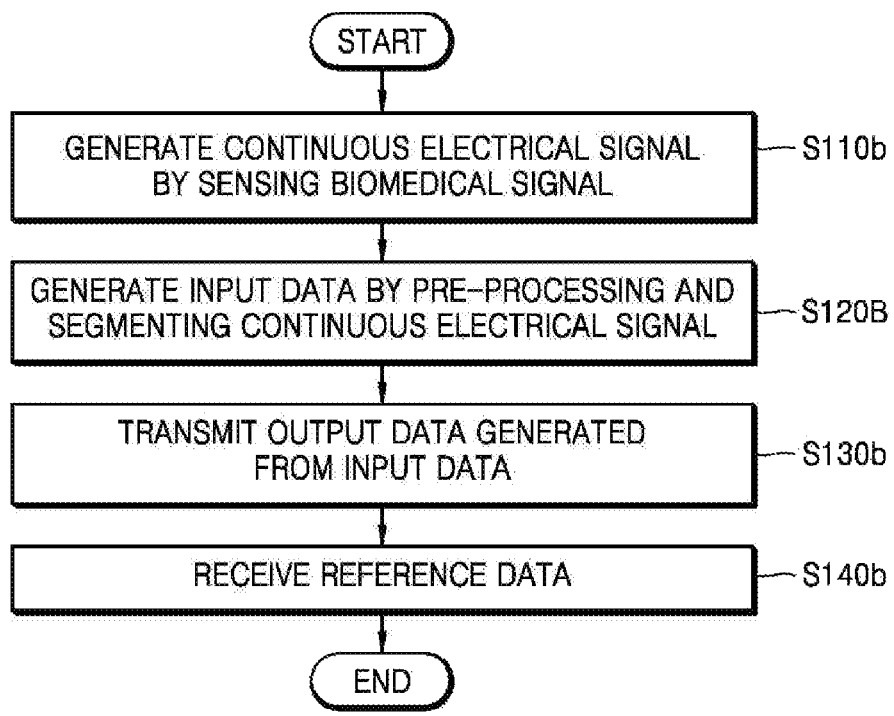
Figure 12C:
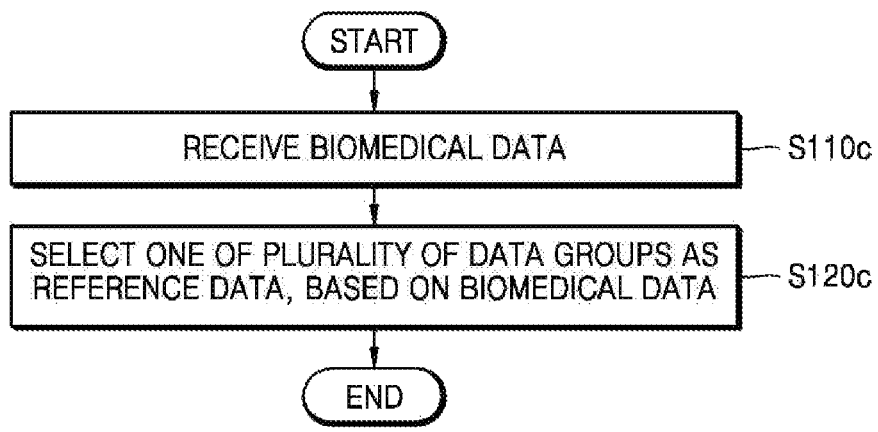
Figure 13:
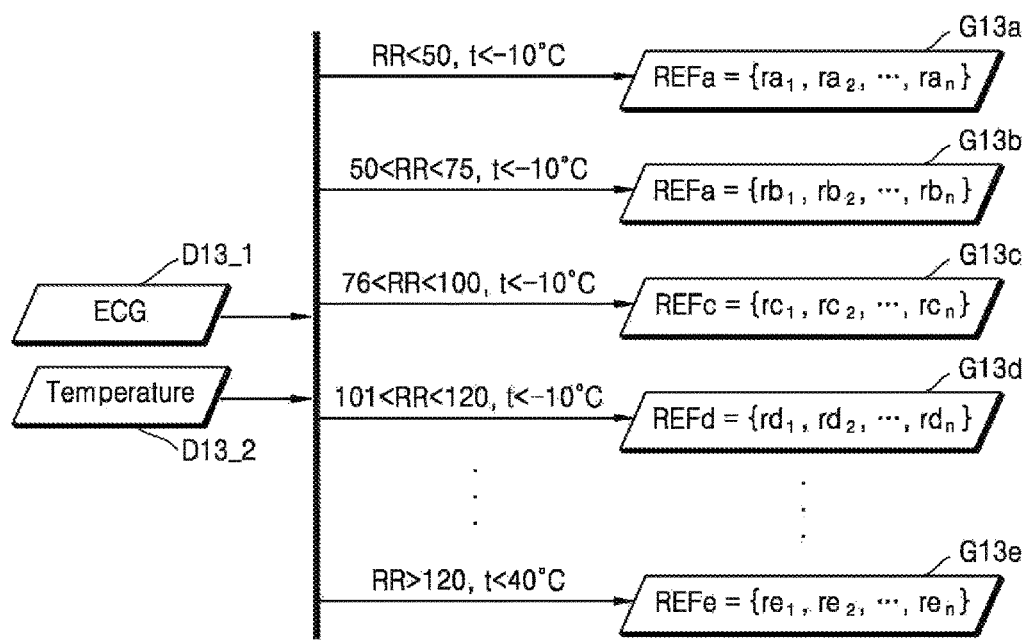
FIG. 13 is a diagram for explaining the example of FIG. 12C.

FIGS. 12A to 12C are flowcharts illustrating examples of operation S100 of FIG. 11, and FIG. 13 is a diagram for explaining the example of FIG. 12C. As described above with reference to FIG. 11, an operation of preparing reference data D_REF may be performed in operation S100 of FIG. 11. Operation S100 may be performed when the monitoring of the biomedical signal S_BIO is started or when the monitoring of the biomedical signal S_BIO is ended. Hereinafter, FIGS. 12A to 12C and FIG. 13 will be described with reference to FIG. 10.

Referring to FIG. 12A, reference data D_REF may be generated in sensor system 200 of FIG. 10, based on statistical data D_STA. To this end, input data D_IN may be collected. As shown in FIG. 12A, an operation of generating a continuous electrical signal S_SEN by sensing a biomedical signal S_BIO may be performed in operation S110a, and an operation of generating input data D_IN by pre-processing and segmenting the continuous electrical signal S_SEN may be performed in operation S120a. Operations S110a and S120a may be repeatedly performed, and generated input data D_IN may be stored in a memory (e.g., memory 220 of FIG. 10).

An operation S130a may include generating statistical data D_STA based on the input data D_IN and storing the generated statistical data D_STA in a memory. For example, a statistics data generation unit included in the data processing unit 230 of FIG. 10 may generate statistical data D_STA including an average, a standard deviation, and the like, based on the input data D_IN stored in the memory 220, and may store the generated statistical data D_STA in memory 220.

An operation S140a may include generating reference data D_REF based the statistical data D_STA. For example, as shown in FIG. 8A, the reference data D_REF may include a series of reference samples, each of which includes an upper limit and a lower limit, and the upper limit and the lower limit of each sample may be generated based on the average and the standard deviation, included in the statistical data D_STA generated in operation S130a.

Referring to FIG. 12B, reference data D_REF may be received from the outside of sensor system 200 of FIG. 10. The reference data D_REF may be generated based on a biomedical signal S_BIO sensed by sensor system 200, and accordingly, sensor system 200 may provide data corresponding to the biomedical signal S_BIO so that the reference data D_REF is generated from the outside of sensor system 200. As shown in FIG. 12B, an operation of generating a continuous electrical signal S_SEN by sensing a biomedical signal S_BIO may be performed in operation S110b, and an operation of generating input data D_IN by pre-processing and segmenting the continuous electrical signal S_SEN may be performed in operation S120b. Next, an operation of transmitting output data D_OUT generated from the input data D_IN to an external device outside of sensor system 200 may be performed in operation S130b. Operations S110b to S130b may be repeatedly performed, and the output data D_OUT generated from the input data D_IN may be transmitted to an external device several times.

An operation S140b may include receiving reference data D_REF. The reference data D_REF may be data generated based on the output data D_OUT transmitted in operation S130b, or may be data generated by a biomedical signal expert such as a medical doctor. The received reference data D_REF may be stored in memory 220 of FIG. 10, and may be used for determining whether an anomaly has occurred in input data D_IN generated by sensing a biomedical signal S_BIO.

Referring to FIG. 12C, reference data D_REF may be prepared by selecting one of a plurality of data groups. As shown in FIG. 12C, an operation of receiving biomedical data may be performed in operation S110c. The biomedical data includes biomedical information of the body 10 of FIG. 1, and sensor system 200 of FIG. 10 may receive external data D_EXT including the biomedical data. For example, the biomedical data may be received from other sensors attached to or implanted in the body 10 of FIG. 1, or may be received from an aggregator (e.g., aggregator 20 of FIG. 1) that communicates with sensor system 200 based on data received from other sensors. Referring to FIG. 13, sensor system 200 may receive biomedical data including, for example, an ECG D13_1 and a temperature D13_2.

An operation S120c may include selecting one of the plurality of data groups as reference data, based on the biomedical data. Referring to FIG. 13, memory 220 of FIG. 10 may store a plurality of data groups G13a to G13e. The data groups G13a to G13e may include reference data REFa to REFe, respectively, and each of the data groups G13a to G13e may correspond to a specific state of a body. For example, the data group G13a may include the reference data REFa including a series of reference samples $ra_1, \ldots,$ and $ra_n$, and may correspond to a state of a body, in which a respiration rate (RR) is less than 50 and a body temperature is less than 10° C. Accordingly, sensor system 200 of FIG. 10 may select one of the plurality of data groups G13a to G13e as the reference data D_REF, based on the ECG D13_1 and the temperature D13_2, received in operation S110c.

Figure 14:
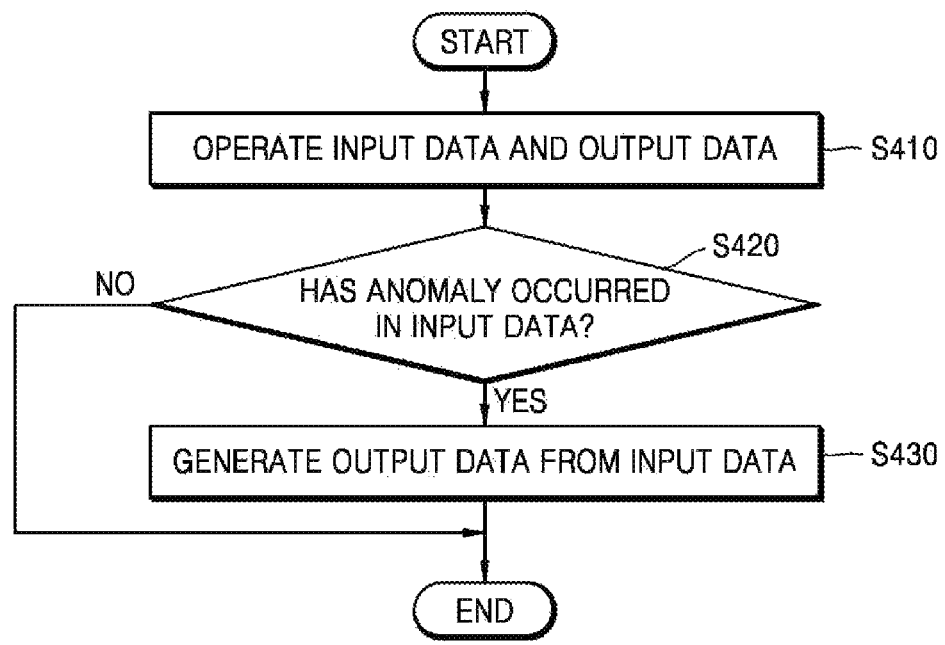
FIG. 14 is a flowchart illustrating an example of operation S400 of FIG. 11.

FIG. 14 is a flowchart illustrating an example of operation S400 of FIG. 11, according to an embodiment. As described above with reference to FIG. 11, an operation of determining whether to transmit input data D_IN, based on the input data D_IN and reference data D_REF, may be performed in operation S400. Hereinafter, FIG. 14 will be described with reference to FIG. 5.

Referring to FIG. 14, an operation 410 may include performing an operation on the input data D_IN and output data D_OUT, and whether an anomaly has occurred in the input data D_IN may be determined in operation S420. For example, operation unit 134 of FIG. 5 may perform an operation on the input data D_IN and the reference data D_REF, as in one of the examples shown in FIGS. 8A to 8C, and may output a determination signal S_DET indicating whether an anomaly has occurred in the input data D_IN.

If it is determined that an anomaly has occurred in the input data D_IN, an operation of generating output data D_OUT from the input data D_IN may be performed in operation S430. For example, in response to an activated determination signal S_DET, output data generation unit 138 of FIG. 5 may generate output data D_OUT by adding a time stamp to received input data D_IN. In addition, in some embodiments, output data generation unit 138 may generate output data D_OUT so as to include a deviation between input data D_IN and reference data D_REF.

FIG. 15 is a diagram that sequentially illustrates examples of operations between a sensor system 300, an aggregator 400, and a storage server 500. Specifically, FIG. 15 illustrates an example of storing output data, which is transmitted from the sensor system 300, in storage server 500. As described above with reference to FIG. 1, sensor system 300 that is attached to or implanted in a body may communicate with aggregator 400 and an access point (e.g., access point 30) via a wireless channel, and may communicate with storage server 500 via the access point and a communication network.

Referring to FIG. 15, in operation S801 sensor system 300 may periodically transmit statistical data to aggregator 400 and/or storage server 500. The statistical data may include statistical information of a biomedical signal sensed by sensor system 300, and aggregator 400 and/or storage server 500 may store or analyze the statistical data. By transmitting only the statistical data to aggregator 400 and/or storage server 500 instead of transmitting all data corresponding to the biomedical signal to aggregator 400 and/or storage server 500, the amount of data that is transmitted by the sensor system 300 via a wireless channel may be remarkably reduced.

Referring to FIG. 15 again, sensor system 300 may transmit output data to aggregator 400 and aggregator 400 may transmit received output data to storage server 500. As shown in FIG. 15, in operation S811, sensor system 300 may determine whether an anomaly has occurred in a biomedical signal. If it is determined that an anomaly has occurred in the biomedical signal, sensor system 300 may transmit output data to aggregator 400 (operation S812), and aggregator 400 may transmit received output data to storage server 500 (operation S813). According to an embodiment, in operation S813, the output data that is transmitted from aggregator 400 to storage server 500 may be encoded. In operation S814, storage server 500 may store received output data.

Referring to FIG. 15 again, sensor system 300 may directly transmit output data to storage server 500. As shown in FIG. 15, in operation S821, sensor system 300 may determine whether an anomaly has occurred in a biomedical signal. If it is determined that an anomaly has occurred in the biomedical signal, sensor system 300 may directly transmit output data to storage server 500 (operation S822). In operation S822, the output data that is transmitted from sensor system 300 to storage server 500 may be encoded. In operation S823, the storage server 500 may store received output data.

Referring to FIG. 15 again, sensor system 300 and aggregator 400 may store output data. As shown in FIG. 15, in operation S831, the sensor system 300 may determine whether an anomaly has occurred in a biomedical signal. If it is determined that an anomaly has occurred in the biomedical signal, sensor system 300 may store output data in a storage device (e.g., memory 120 of FIG. 3) included in sensor system 300 (operation S832), and may transmit the output data to aggregator 400 (operation S833). Aggregator 400 may store received output data in a storage device (e.g., a memory device) included in aggregator 400 (operation S834), and may transmit the output data to storage server 500 (operation S835). In operation S836, storage server 500 may store received output data.

FIG. 16 is a diagram that sequentially illustrates examples of operations between a plurality of sensor systems, i.e., first and second sensor systems 301 and 302, and aggregator 400. Specifically, FIG. 16 illustrates an operation in which aggregator 400 prepares reference data based on biomedical data received from first and second sensor systems 301 and 302 and transmits the prepared reference data to first and second sensor systems 301 and 302.

Each of first and second sensor systems 301 and 302 shown in FIG. 16 may include a receiver for receiving data via a wireless channel. Referring to FIG. 16, in operation S851, aggregator 400 may request output data from first and second sensor systems 301 and 302. In operation S852, first sensor system 301 may transmit first output data to aggregator 400 in response to the request of aggregator 400. In operation S853, second sensor system 302 may transmit second output data to aggregator 400 in response to the request of aggregator 400. The first output data in operations S852 is data generated when first sensor system 301 senses a biomedical signal, and the second output data in operations S853 is data generated when second sensor system 302 senses a biomedical signal. The first and second output data may be used for generating reference data. Operations S851 to S853 may be repeated over and over.

In operation S854, aggregator 400 may prepare reference data. In other words, aggregator 400 may prepare first and second reference data corresponding to first and second sensor systems 301 and 302, respectively, which sense different biomedical signals. For example, as will be described later with reference to FIG. 17A, aggregator 400 may generate reference data based on the first and second output data. In addition, as will be described later with reference to FIG. 17B, aggregator 400 may provide the first and second output data to a computing server and receive reference data from the computing server. Details of operation S854 will be described later with reference to FIGS. 17A and 17B.

In operation S855, aggregator 400 may transmit the first reference data to first sensor system 301, and in operation S856, aggregator 400 may transmit the second reference data to second sensor system 302.

In operation S861, first sensor system 301 may transmit the first output data to the aggregator 400, and in operation S871, second sensor system 302 may transmit the second output data to aggregator 400. First and second sensor systems 301 may use the first and second reference data, respectively, to determine whether an anomaly has occurred in a biomedical signal (or input data generated from the biomedical signal). If it is determined that an anomaly has occurred in a biomedical signal, first and second sensor systems 301 may transmit data corresponding to the biomedical signal to aggregator 400 as output data.

Figure 17A:
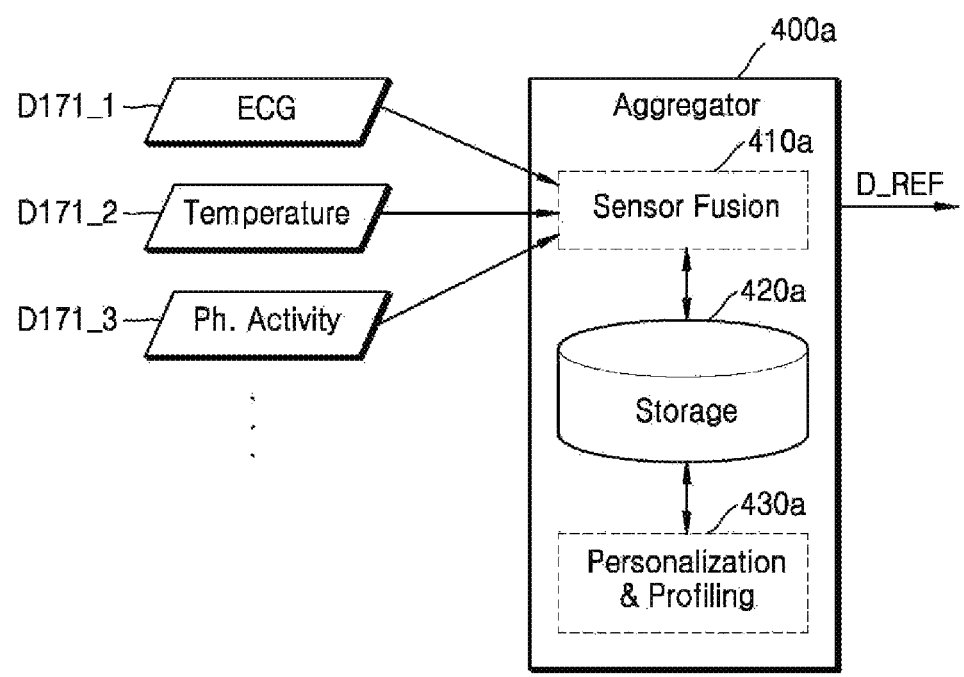
FIGS. 17A and 17B are diagrams illustrating examples of operation S854 of FIG. 16.
Figure 17B:
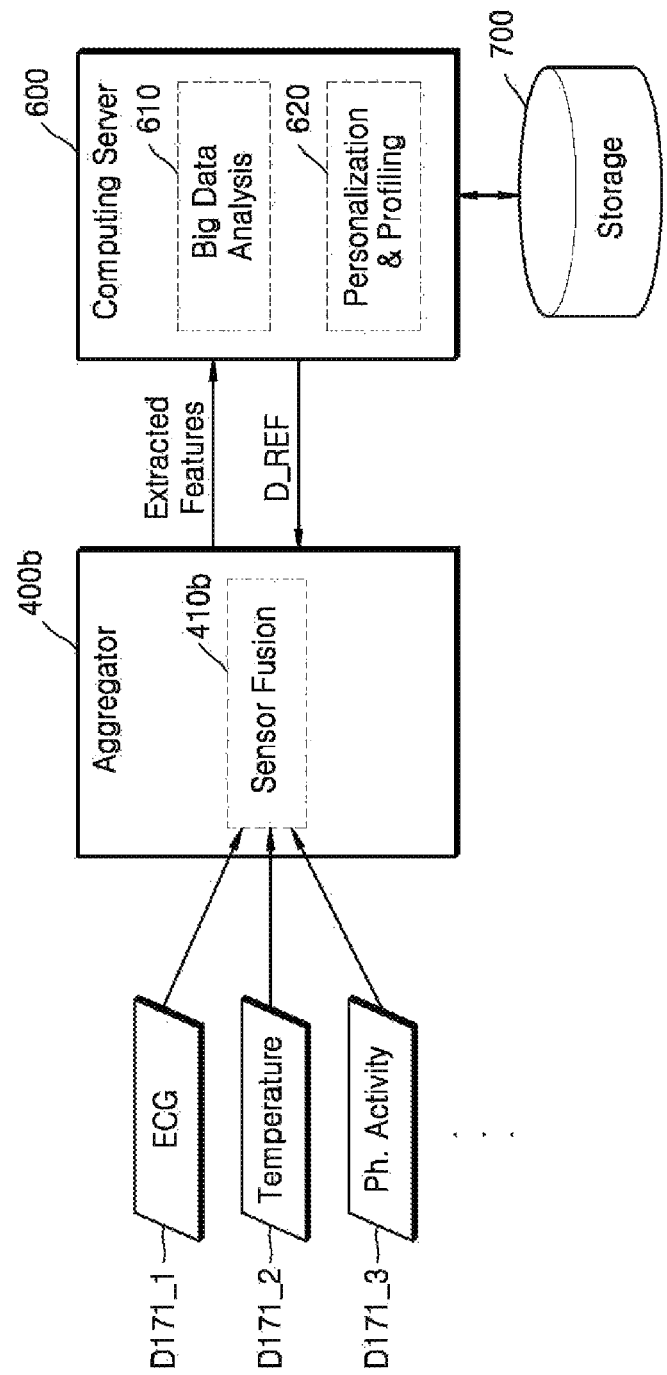

FIGS. 17A and 17B are diagrams illustrating examples of operation S854 of FIG. 16. Specifically, FIG. 17A illustrates an example in which reference data D_REF is generated in an aggregator 400a, and FIG. 17B illustrates an example in which reference data D_REF is generated in a computing server 600 that communicates with aggregator 400a. As described above with reference to FIG. 16, in operation S854 of FIG. 16, reference data D_REF may prepared by aggregator 400. In FIGS. 17A and 17B, data received from a plurality of sensors may include an ECG D171_1, a temperature D171_2, and a body activity rate D171_3.

Referring to FIG. 17A, aggregator 400a may include a sensor fusion module 410a, a storage device 420a, and a personalization & profiling module 430a. Sensor fusion module 410a and personalization & profiling module 430a may be hardware modules or software modules.

Sensor fusion module 410a may remove inaccuracy, which may occur when only a single sensor is used, by intelligently combining data from a plurality of sensor systems. Sensor fusion module 410a may extract features from data (i.e., biomedical data) that are received from the plurality of sensor systems, and the extracted features may be stored in storage device 420a. The features stored in storage device 420a may be referred to by personalization & profiling module 430a.

Personalization & profiling module 430a enables adaptively generating reference data D_REF. For example, the personalization & profiling module may adjust the reference data D_REF according to a behavior pattern, such as a sleep state, an awakening state, and an exercise state, based on received biomedical data D171_1, D171_2, and D171_3 (or data generated by sensor fusion module 410a) as well as information, such as a position and an ambient temperature, acquired by aggregator 400a. Accordingly, whether an anomaly has occurred in a biomedical signal may be more accurately determined by a sensor system (e.g., sensor systems 301 and 302 of FIG. 16). Personalization & profiling module 430a may access storage device 420a, and may refer to information about relation between a plurality of parameters stored in storage device 420a.

Referring to FIG. 17B, aggregator 400b may include a sensor fusion module 410b. Similar to the example of FIG. 17A, sensor fusion module 410b may extract features from received biomedical data, and may provide extracted features to computing server 600.

Computing server 600 may include a big data analysis module 610 and a personalization & profiling module 620, and may communicate with a storage device 700. Big data analysis module 610 and personalization & profiling module 620 may be hardware modules or software modules. Big data analysis module 610 may analyze extracted features, based on big data stored in storage device 700. Also, big data analysis module 610 may generate information, which is necessary to generate the reference data D_REF, through machine learning. Similar to the example of FIG. 17A, personalization & profiling module 620 enables adaptively generating the reference data D_REF.

Figure 18:
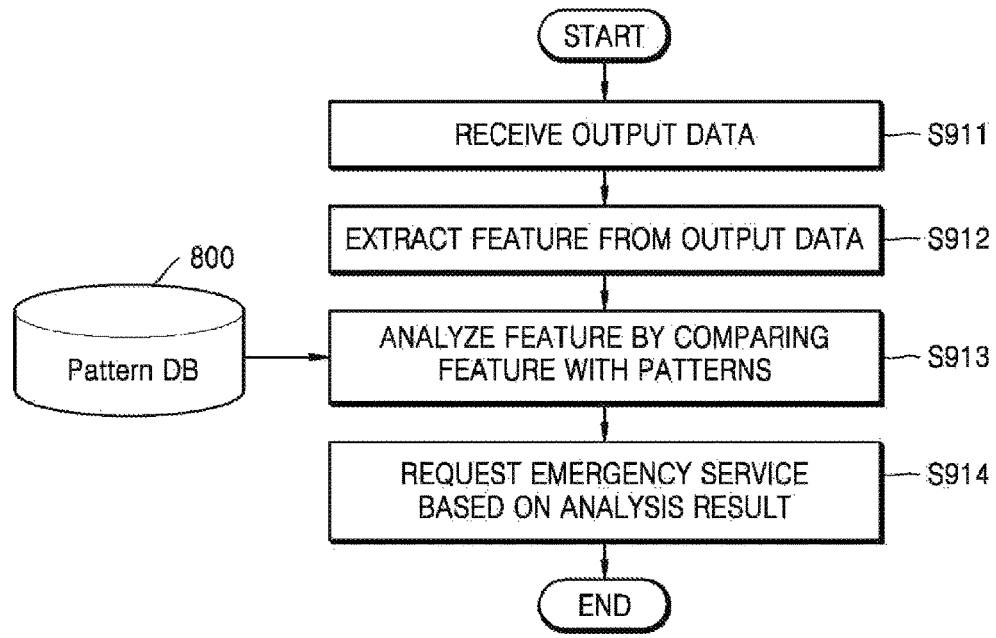
FIG. 18 is a flowchart illustrating an example of a method of monitoring a biomedical signal.

FIG. 18 is a flowchart illustrating an example of a method of monitoring a biomedical signal. Specifically, FIG. 18 is a flowchart illustrating an example of requesting an emergency service when a severe anomaly occurs in a biomedical signal sensed by a sensor system. Although FIG. 18 illustrates an example that is performed in an aggregator (e.g., aggregator 20 of FIG. 1) communicating with a sensor system, the sensor system may also perform a method that is similar to the example illustrated in FIG. 18. Hereinafter, FIG. 18 will be described with reference to FIG. 1.

Referring to FIG. 18, in operation S911 aggregator 20 of FIG. 1 may receive output data. In operation S912, aggregator 20 may extract a feature from the output data. In operation S913, aggregator 20 may analyze the feature by comparing the feature with patterns stored in a pattern database (DB) 800. For example, aggregator 20 may analyze an extracted pattern to determine that it is consistent with a pattern corresponding to an emergency state of the body 10 of FIG. 1 among a plurality of patterns.

In operation S914, aggregator 20 may perform an operation of requesting an emergency service, based on an analysis result. For example, aggregator 20 may transmit a signal, which requests an emergency service, to user terminal 80 installed in an emergency medical center via access point 30 and communication network 50.

Figure 19:
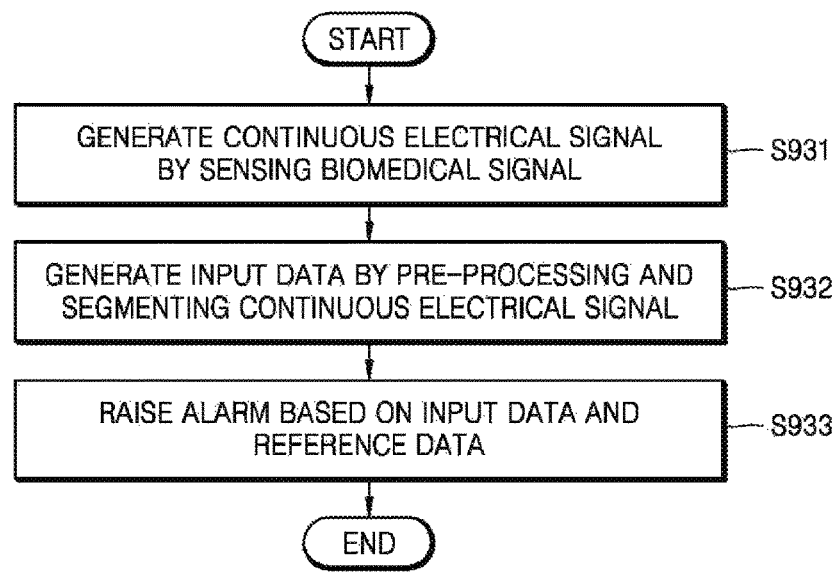
FIG. 19 is a flowchart illustrating an example of a method of monitoring a biomedical signal.

FIG. 19 is a flowchart illustrating an example of a method of monitoring a biomedical signal. Specifically, FIG. 19 illustrates an example in which when an anomaly occurs in a biomedical signal sensed by a sensor system, and the sensor system outputs a signal, which may be sensed from the outside of the sensor system, to immediately report that an anomaly has occurred in the biomedical signal. As described above with reference to FIG. 10, outputting a signal that may be sensed from the outside of the sensor system may help the sensor system to be disposed in an appropriate location, as well as provide a function of immediately reporting an anomaly of a biomedical signal. Hereinafter, FIG. 19 will be described with reference to FIG. 10.

In operation S931, an operation of generating a continuous electrical signal by sensing a biomedical signal may be performed. For example, sensor module 210 of FIG. 10 may convert a biomedical signal S_BIO into a continuous electrical signal S_SEN to output the continuous electrical signal S_SEN.

In operation S932, an operation of generating input data by pre-processing and segmenting the continuous electrical signal may be performed. For example, the input data generation unit included in data processing unit 230 of FIG. 10 may generate input data by pre-processing and segmenting the continuous electrical signal S_SEN.

In operation S933, an operation of raising an alarm based on the input data and reference data may be performed. For example, the operation unit included in data processing unit 230 of FIG. 10 may perform an operation on the input data and the reference data, and may generate a determination signal S_DET indicating whether an anomaly has occurred in the input data. Alarm module 270 of FIG. 10 may receive the determination signal S_DET from data processing unit 230, and may output at least one selected from an image, light, vibration, and sound to the outside of sensor system 200 when the determination signal S_DET is activated.

While the inventive concept has been particularly shown and described with reference to embodiments thereof, it will be understood that various changes in form and details may be made therein without departing from the spirit and scope of the following claims.

What is claimed is:

1. A sensor system for monitoring a biomedical signal, the sensor system comprising:
    a sensor module configured to sense the biomedical signal and output a continuous electrical signal;
    a memory configured to store reference data which is used for determining whether an anomaly has occurred in input data which is generated from the continuous electrical signal;
    a transmitter configured to transmit output data via a wireless channel to an external device; and
    a data processing unit configured to determine whether to transmit the input data, which is generated from the continuous electrical signal, via the transmitter as the output data, based on the input data and the reference data.

2. The sensor system of claim 1, wherein the data processing unit comprises:
    an input data generation unit configured to generate the input data by pre-processing and segmenting the continuous electrical signal;
    an operation unit configured to perform an operation on the input data and the reference data as operands to detect whether the input data includes the anomaly; and
    an output data generation unit configured to generate the output data from the input data in response to detecting the anomaly in the input data.

3. The sensor system of claim 2, wherein, in response to the anomaly occurring in the input data, the output data generation unit generates the output data by adding a time stamp to the input data.

4. The sensor system of claim 2, wherein the data processing unit further comprises a statistics data generation unit configured to generate statistical data of the biomedical signal based on the input data, and
    wherein the output data generation unit generates output data from the statistical data during a predetermined period.

5. The sensor system of claim 2, wherein the input data generation unit comprises:
    a filtering unit configured to filter the continuous electrical signal;
    a synchronizing unit configured to synchronize an output signal of the filtering unit to the reference data;
    an offset adjusting unit configured to adjust an offset of an output signal of the synchronizing unit; and
    a segmentation unit configured to segment an output signal of the offset adjusting unit into sections corresponding to the reference data, and generate the input data.

6. The sensor system of claim 2, wherein the reference data comprises a series of reference samples aligned according to time, and
    wherein the input data comprises a series of input samples corresponding to the series of reference samples.

7. The sensor system of claim 6, wherein each of the series of reference samples comprises an upper limit and a lower limit of an input sample corresponding to the reference sample, and
    wherein the operation unit detects the anomaly in the input data in response to a number of the input samples which are out of range between the upper limit and the lower limit among the series of input samples exceeding a predetermined number.

8. The sensor system of claim 7, wherein the reference samples include a series of the reference samples comprising upper limits having a same value as each other and lower limits having a same value as each other.

9. The sensor system of claim 6, wherein each of the series of reference samples comprises an average and a deviation of an input sample corresponding to the reference sample, and
    wherein the operation unit detects the anomaly in the input data in response to a number of the input samples, which differ from the average by more than the deviation, among the series of input samples, exceeding a predetermined number.

10. The sensor system of claim 6, wherein the output data generation unit generates the output data from differences between the input samples and averages thereto, or generates the output data by compressing the differences.

11. The sensor system of claim 6, wherein each of the series of reference samples comprises an average and a weight of an input sample corresponding to the reference sample, and
wherein the operation unit calculates a multiplication of the weight and a difference between the input sample and the average thereto with respect to input samples of a predetermined number among the input samples, and detects the anomaly in the input data in response to the sum of multiplication values corresponding to the input samples of the predetermined number exceeding a predetermined value.

12. The sensor system of claim 11, wherein the weight is inversely proportional to a standard deviation of the input sample.

13. The sensor system of claim 2, further comprising an alarm module configured to output at least one selected from an image, light, vibration, and sound, in response to detecting the anomaly in the input data.

14. A method of monitoring a biomedical signal by at least one sensor system and an aggregator, which can communicate with each other via a wireless channel, the method comprising:
generating, by the at least one sensor system, input data by sensing the biomedical signal;
determining, by the at least one sensor system, whether to transmit the input data to the aggregator as output data, based on the input data and previously stored reference data which is used for determining whether an anomaly has occurred in the input data;
transmitting, by the at least one sensor system, the output data to the aggregator; and
transmitting, by the aggregator, the output data to a storage server or a terminal device via a communication network after receiving the output data.

15. The method of claim 14, wherein the determining, by the at least one sensor system, whether to transmit the input data comprises:
performing an operation on the input data and the reference data as operands to detect whether the input data includes the anomaly; and
generating the output data from the input data in response to detecting the anomaly in the input data.

16. The method of claim 14, further comprising:
transmitting, by the at least one sensor system, the input data to the aggregator as the output data when the monitoring of the biomedical signal is started,
generating, by the aggregator, the reference data based on output data received from the at least one sensor system; and
transmitting, by the aggregator, the reference data to the sensor system.

17. The method of claim 14, further comprising:
extracting, by the aggregator, a feature from the output data;
analyzing, by the aggregator, the output data by comparing the feature with predetermined pattern data; and
transmitting, by the aggregator, a request for an emergency service to an emergency service system via the communication network, based on a result obtained by analyzing the output data.

18. The method of claim 14, further comprising outputting, by the aggregator, at least one selected from an image, light, vibration, and sound to the outside, based on the result obtained by analyzing the output data.

19. The method of claim 14, wherein the transmitting, by the aggregator, of the output data to a storage server or a terminal device comprises:
encoding the output data; and
transmitting encoded output data to the storage server or the terminal device via the communication network.

20. The method of claim 14, wherein the aggregator comprises a mobile phone.

* * * * *